US012002115B2

(12) United States Patent
Bull et al.

(10) Patent No.: US 12,002,115 B2
(45) Date of Patent: Jun. 4, 2024

(54) DIGITAL MODELING AND TRACKING OF AGRICULTURAL FIELDS FOR IMPLEMENTING AGRICULTURAL FIELD TRIALS

(71) Applicant: CLIMATE LLC, Saint Louis, MO (US)

(72) Inventors: Jason Kendrick Bull, Wildwood, MO (US); Nicholas Charles Cizek, Stanford, CA (US); Brandon Rinkenberger, Chesterfield, MO (US); Thomas Gene Ruff, Wildwood, MO (US); Doug Sauder, Livermore, CA (US)

(73) Assignee: CLIMATE LLC, Saint Louis, MO (US)

( * ) Notice: Subject to any disclaimer, the term of this patent is extended or adjusted under 35 U.S.C. 154(b) by 0 days.

(21) Appl. No.: 18/111,795

(22) Filed: Feb. 20, 2023

(65) Prior Publication Data

US 2023/0206352 A1 Jun. 29, 2023

Related U.S. Application Data

(63) Continuation of application No. 17/458,099, filed on Aug. 26, 2021, now Pat. No. 11,587,186, which is a
(Continued)

(51) Int. Cl.
*G06Q 50/02* (2012.01)
*A01B 69/00* (2006.01)
(Continued)

(52) U.S. Cl.
CPC ............ *G06Q 50/02* (2013.01); *A01B 79/005* (2013.01); *F24F 11/49* (2018.01); *G01C 11/025* (2013.01);
(Continued)

(58) Field of Classification Search
CPC .............. G06Q 50/02; G06Q 10/06393; A01B 79/005; A01B 69/00; F24F 11/49;
(Continued)

(56) References Cited

U.S. PATENT DOCUMENTS 5,961,573 A 10/1999 Hale et al.
6,058,351 A 5/2000 McCauley
(Continued)

FOREIGN PATENT DOCUMENTS

EP 3923231 12/2021
WO WO2016/200699 12/2016
WO WO-2017148818 A1 * 9/2017 ........... A01B 79/005

OTHER PUBLICATIONS

M. Ayaz, M. Ammad-Uddin, Z. Sharif, A. Mansour and E.-H. M. Aggoune, "Internet-of-Things (IoT)-Based Smart Agriculture: Toward Making the Fields Talk," in IEEE Access, vol. 7, pp. 129551-129583, 2019, doi: 10.1109/ACCESS.2019.2932609. (Year: 2019).*
(Continued)

*Primary Examiner* — Crystol Stewart
(74) *Attorney, Agent, or Firm* — Harness, Dickey & Pierce, P.L.C.

(57) ABSTRACT

A system for implementing a trial in one or more fields is provided. In an embodiment, a agricultural intelligence computing system receives field data for a plurality of agricultural fields. Based, at least in part, on the field data for the plurality of agricultural fields, the agricultural intelligence computing system identifies one or more target agricultural fields. The agricultural intelligence computing system sends, to a field manager computing device associated with the one or more target agricultural fields, a trial participation request. The server receives data indicating acceptance of the trial participation request from the field manager computing device. The server determines one or more locations on the one or more target agricultural fields
(Continued)

for implementing a trial and sends data identifying the one or more locations to the field manager computing device.

16 Claims, 17 Drawing Sheets

Related U.S. Application Data continuation of application No. 16/108,002, filed on Aug. 21, 2018, now Pat. No. 11,145,007.

(60) Provisional application No. 62/548,396, filed on Aug. 21, 2017.

(51) Int. Cl.
| | | |
|---|---|---|
| *A01B 79/00* | (2006.01) | |
| *F24F 11/49* | (2018.01) | |
| *G01C 11/02* | (2006.01) | |
| *G01N 33/24* | (2006.01) | |
| *G06N 7/01* | (2023.01) | |
| *G06Q 10/0639* | (2023.01) | |

(52) U.S. Cl.
CPC .............. *G01N 33/24* (2013.01); *G06N 7/01* (2023.01); *G06Q 10/06393* (2013.01); *A01B 69/00* (2013.01); *Y02A 40/10* (2018.01)

(58) Field of Classification Search
CPC ...... G01C 11/025; G01N 33/24; G06N 7/005; G06N 3/126; Y02A 40/10
See application file for complete search history.

(56) References Cited

U.S. PATENT DOCUMENTS

| | | |
|---|---|---|
| 10,104,836 B2 | 10/2018 | Jamison |
| 11,145,007 B2 | 10/2021 | Ruff et al. |
| 11,587,186 B2 | 2/2023 | Ruff et al. |
| 2006/0074700 A1 | 4/2006 | Ricketts |
| 2013/0231968 A1 | 9/2013 | Willness |
| 2014/0035752 A1* | 2/2014 | Johnson ............... A01B 79/005 340/601 |
| 2014/0067745 A1 | 3/2014 | Avey et al. |
| 2014/0089045 A1 | 3/2014 | Johnson |
| 2015/0185196 A1 | 7/2015 | Coram et al. |
| 2016/0057922 A1* | 3/2016 | Freiberg ............... A01B 79/005 703/11 |
| 2016/0078569 A1 | 3/2016 | Ethington et al. |
| 2016/0085943 A1 | 3/2016 | De Vries et al. |
| 2016/0202227 A1 | 7/2016 | Mathur et al. |
| 2016/0232621 A1 | 8/2016 | Ethington et al. |
| 2016/0314280 A1 | 10/2016 | Fusari et al. |
| 2017/0041407 A1 | 2/2017 | Wilbur et al. |
| 2017/0161560 A1 | 6/2017 | Itzhaky et al. |
| 2017/0196171 A1 | 7/2017 | Xu et al. |
| 2018/0314949 A1 | 11/2018 | Bender et al. |
| 2018/0336410 A1* | 11/2018 | Posselius ............ A01B 49/027 |
| 2018/0365775 A1 | 12/2018 | You |
| 2019/0050948 A1* | 2/2019 | Perry ...................... G06F 30/27 |
| 2019/0057461 A1 | 2/2019 | Ruff et al. |
| 2021/0374161 A1 | 12/2021 | Marvaniya et al. |

OTHER PUBLICATIONS

Franzel et al., Participatory On-Farm Technology Testing: The Suitability of Different Types of Trails for Different Objectives, 2002, Bellon et al., Quantative Analysis of Data from Participatory Methods in Plant Breeding, p. 1-8 (Year: 2002).
Snapp, Quanitfying Farmer Evaluation of Technologies: The Mother and Baby Trail Design, 2002, Bellon et al., Quanitive Analysis of Data from Participatory Methods in Plant Breeding, p. 9-17, (Year: 2002).
S Kumar, M Shamim, M Bansal, B. Gangwar and R P. Aggarwal. "Computational modeling and emerging trend in agriculture," 2015 $2^{nd}$ International Conference on Computing Sustainable Global Development (INDIACom), 2015, pp. 1156-1160. (Year: 2015).
Wozniak et al., "Regulation of Agricultural Biotechnology: The United States and Canada." Springer, dated 2013.
Norman et al. "The Farming Systems Approach to Development and Appropriate Technology Generation", FAO, dated 1995, 13 pages.
U.S. Appl. No. 17/458,099, filed Aug. 26, 2021, Ruff et al.
U.S. Appl. No. 16/108,002, filed Aug. 21, 2018, Ruff et al.
U.S. Appl. No. 17/458,099, filed Aug. 25, 2021, Ruff et al.
U.S. Appl. No. 16/667,177: (a) Office Action dated May 10, 2022; (b) Office Action dated Oct. 11, 2022; and (c) Notice of Allowance dated Feb. 15, 2023. The instant application is a continuation of U.S. Appl. No. 16/667,177.
U.S. Appl. No. 16/108,002: (a) Office Action dated Oct. 20, 2020; (b) Office Action dated Apr. 6, 2021; and (c) Notice of Allowance dated Jun. 10, 2021. The instant application has the same priority as U.S. Appl. No. 16/108,002.
PCT/US2018/047397: PCT International Search Report and Written Opinion of PCT dated Jan. 3, 2020, which has the same priority claim as the instant application.
BR112020003688-9: Office Action dated Jun. 27, 2022. The Office action is not in the English language. An English language translation is provided for reference. The instant application and BR112020003688-9 have a priority claim in common.
BR122021024395-6: Office Action dated Jun. 27, 2022. The Office action is not in the English language. An English translation is provided for reference. The instant application and BR122921924395-6 have a priority claim in common.
CA3073348: (a) Office Action dated Apr. 19, 2021; and (b) Notice of Allowance dated May 6, 2022. The instant application and CA3073348 have a priority claim in common.
CN201880068566.4: (a) Office Action dated Jun. 9, 2021; and (b)Office Action dated Feb. 21, 2022. The instant application and CN201880068566.4 have a priority claim in common.
EP 18847900.0: (a) Extended European Search Report dated Jul. 13, 2021; and (b) Examination Report dated May 19, 2023. The instant application and EP18847900.0 have a priority claim in common.

* cited by examiner

Fig. 2
(a)
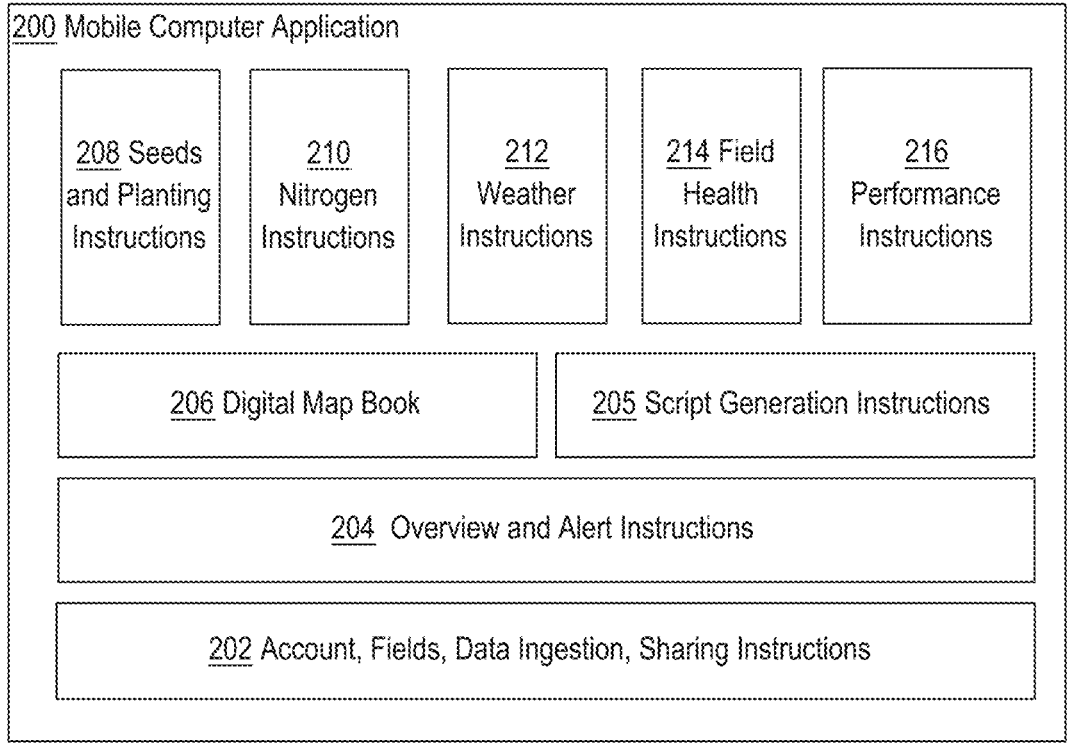
(b)
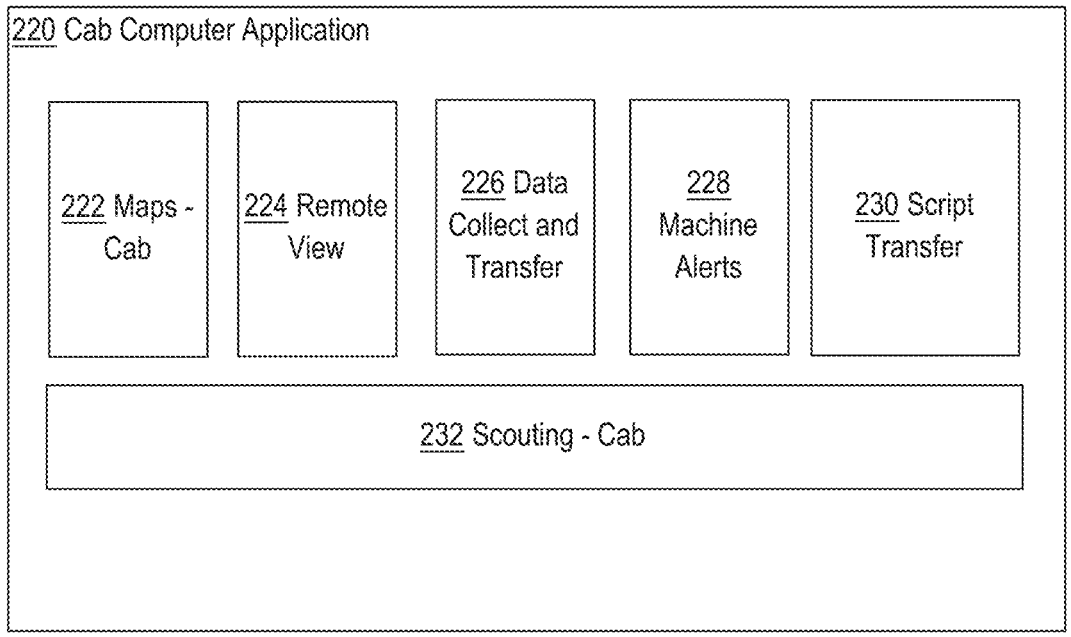

Data Manager

Nitrogen | Planting | Practices | Soil

| Planting 1(4 Fields) | Planting 2(0 Fields) | Planting 3(0 Fields) | Planting 4(1 Fields) | Add New Planting Plan |
| --- | --- | --- | --- | --- |
| Crop Corn Product | Crop Corn Product | Crop Corn Product | Crop Corn Product | |
| Plant Date: 2016-04-12 | Plant Date: 2016-04-15 | Plant Date: 2016-04-13 | Plant Date: 2016-04-13 | |
| ILU 112 \| Pop: 34000 | ILU 83 \| Pop: 34000 | ILU 83 \| Pop: 34000 | ILU 112 \| Pop: 34000 | |
| Edit   Apply | Edit   Apply | Edit   Apply | Edit   Apply | |

| | CROP | PLANTED ACRES | PRODUCT | RELATIVE MATURITY | TARGET YIELD | POPULATION(AVG) | PLA |
| --- | --- | --- | --- | --- | --- | --- | --- |
| ☐ Select All | | | | | | | |
| ☐ Ames, IA 1  Corn \| 100 \| Boone, IA | Corn | --- | DMC82-M | 112 | 160 | 34000 | Apr |
| ☐ Austin, MN 1  Corn \| 100 \| Fredricks, MN | Corn | --- | DMC82-M | 114 | 160 | 36000 | Apr |
| ☐ Boone, IN 1  Corn \| 100 \| Boone, IA | Corn | --- | DMC82-M | 112 | 150 | 34000 | Apr |
| ☐ Champaign 1  Corn \| 100 \| Champaign, IL | Corn | --- | --- | 112 | 200 | 34000 | Apr |
| ☐ E Nebraska 1  Corn \| 100 \| Burt, NE | Corn | --- | --- | 112 | 160 | 34000 | Apr |

FIG. 6

DIGITAL MODELING AND TRACKING OF AGRICULTURAL FIELDS FOR IMPLEMENTING AGRICULTURAL FIELD TRIALS

CROSS-REFERENCE TO RELATED APPLICATIONS

This application claims the benefit under 35 U.S.C. § 120 as a continuation of U.S. patent application Ser. No. 17/458,099, filed Aug. 26, 2021, which is a continuation of U.S. patent application Ser. No. 16/108,002, filed Aug. 21, 2018, which claims the benefit under 35 U.S.C. § 119(e) of provisional application 62/548,396, filed Aug. 21, 2017, the entire contents of which are hereby incorporated by reference for all purposes as if fully set forth herein. The applicants hereby rescind any disclaimer of claim scope in the parent applications or the prosecution history thereof and advise the USPTO that the claims in this application may be broader than any claim in the parent applications.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright or rights whatsoever. © 2021 The Climate Corporation.

FIELD OF THE DISCLOSURE

The present disclosure relates to digital computer modeling and tracking of agricultural fields. Specifically, the present disclosure relates to modeling benefits to an agricultural field of performing particular practices, identifying locations for implementing trials of the particular practices, and tracking the performance of the particular practices.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Field managers are faced with a wide variety of decisions to make with respect to the management of agricultural fields. These decisions range from determining what crop to plant, which type of seed to plant for the crop, when to harvest a crop, whether to perform tillage, irrigation, application of pesticides, application of fungicides, and application of fertilizer, and what types of pesticides, fungicides, and fertilizers to apply.

Often, improvements may be made to the management practices of a field by using different hybrid seeds, applying different products to the field, or performing different management activities on the field. These improvements may not be readily identifiable to a field manager working with only information about their own field. Thus, it is beneficial for a computer system which obtains information regarding a plurality of fields to identify improvements to planting practices, management practices, or application practices.

While recommended improvements may be useful for agricultural fields, they can be risky to implement. Where a field manager can feel assured that the field manager's practices will produce a particular result, the field manager may not feel assured that following the recommendation would lead to a benefit.

Even if a field manager agrees to follow a recommendation, the field manager would not be able to quantify whether benefits achieved are due to the different planting, application, or management practices or due to one or more outside factors such as favorable weather. Thus, without being able to quantify the benefits of particular new practices, a field manager is unable to determine whether the practices should be used in future years.

Thus, there is a need for a method of identifying fields that could benefit from changes in agricultural practices and developing trials that can demonstrate the value in the changes to the agricultural practices.

SUMMARY

The appended claims may serve as a summary of the disclosure.

BRIEF DESCRIPTION OF THE DRAWINGS

In the drawings:

FIG. 2 illustrates two views of an example logical organization of sets of instructions in main memory when an example mobile application is loaded for execution.

FIG. 6 depicts an example embodiment of a spreadsheet view for data entry.

DETAILED DESCRIPTION

Figure 1:
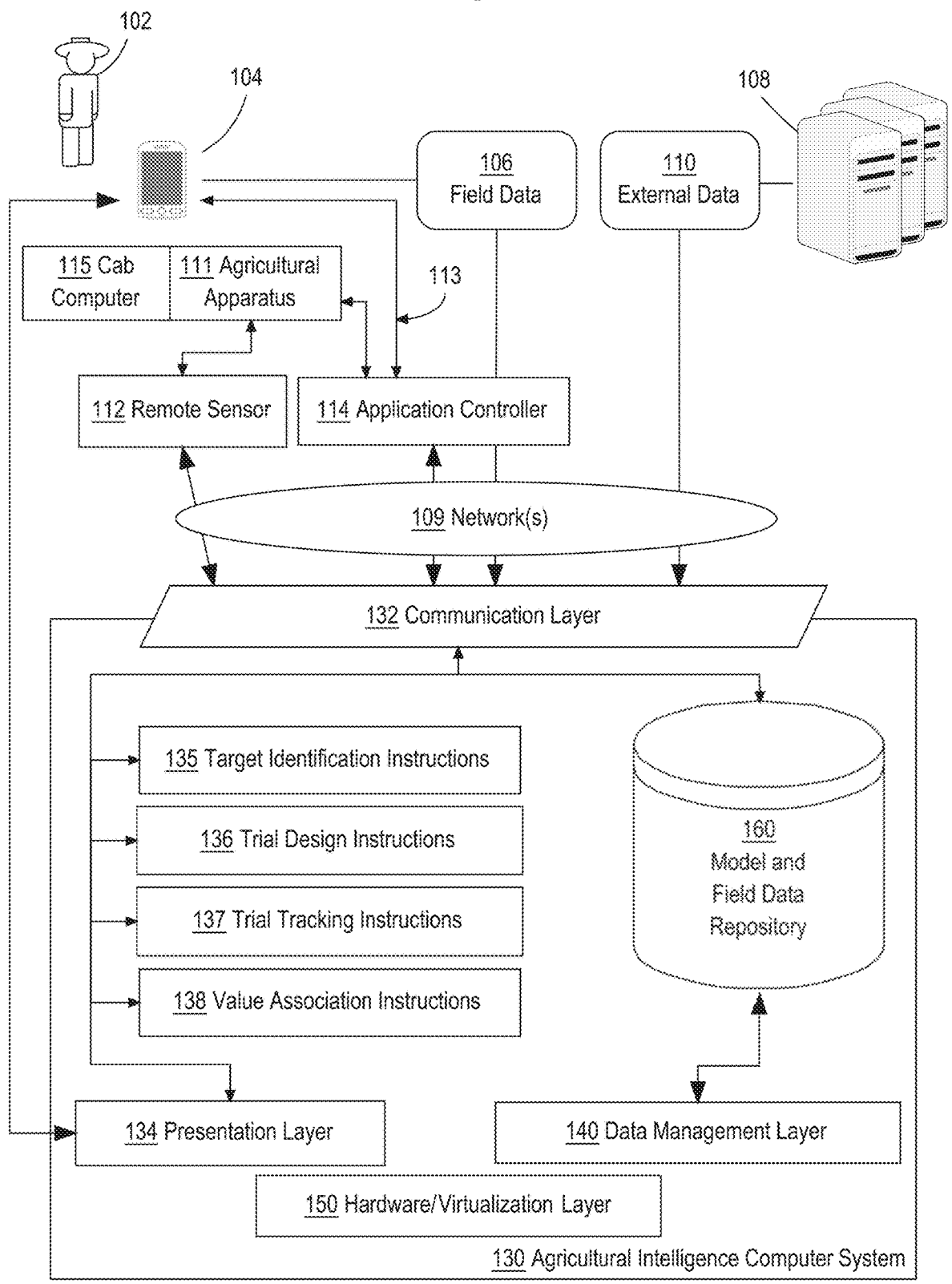
FIG. 1 illustrates an example computer system that is configured to perform the functions described herein, shown in a field environment with other apparatus with which the system may interoperate.

In the following description, for the purposes of explanation, numerous specific details are set forth in order to provide a thorough understanding of the present disclosure. It will be apparent, however, that embodiments may be practiced without these specific details. In other instances, well-known structures and devices are shown in block diagram form in order to avoid unnecessarily obscuring the present disclosure. Embodiments are disclosed in sections according to the following outline:

1. GENERAL OVERVIEW
2. EXAMPLE AGRICULTURAL INTELLIGENCE COMPUTER SYSTEM
  2.1. STRUCTURAL OVERVIEW
  2.2. APPLICATION PROGRAM OVERVIEW
  2.3. DATA INGEST TO THE COMPUTER SYSTEM
  2.4. PROCESS OVERVIEW—AGRONOMIC MODEL TRAINING
  2.5. IMPLEMENTATION EXAMPLE—HARDWARE OVERVIEW
3. FUNCTIONAL OVERVIEW
4. PROVIDED FIELD DATA
5. TARGET IDENTIFICATION
6. TRIAL DESIGN
7. FIELD MANAGER COMPUTING DEVICE COMMUNICATION
8. VALUE ASSOCIATION
9. BENEFITS OF CERTAIN EMBODIMENTS
10. EXTENSIONS AND ALTERNATIVES

1. General Overview

Systems and methods for implementing trials in one or more fields are described herein. In an embodiment, an agricultural intelligence computer system is communicatively coupled to a plurality of field manager computing devices. The agricultural intelligence computer system receives field data for a plurality of agricultural fields and uses the field data to identify fields which would benefit from performing a particular trial. The agricultural intelligence computer system sends a trial participation request to a field manager computing device associated with an identified field which guarantees a particular benefit for participating in the trial. If the field manager computing device agrees to participate in the trial, the agricultural intelligence computer system identifies locations on the identified field for implementing the trial and sends the data to the field manager computing device. The agricultural intelligence computer system may track practices on the identified field to determine whether the identified field is in compliance with the trial. The agricultural intelligence computer system may additionally receive data identifying results of the trial and use the data to compute one or more benefits of the trial.

In an embodiment, a method comprises receiving, at a agricultural intelligence computer system, field data for a plurality of agricultural fields; based, at least in part, on the field data for the plurality of agricultural fields, identifying one or more target agricultural fields; sending, to a field manager computing device associated with the one or more target agricultural fields, a trial participation request; receiving, from the field manager computing device, data indicating acceptance of the trial participation request; determining one or more locations on the one or more target agricultural fields for implementing a trial; sending data identifying the one or more locations to the field manager computing device; receiving application data for the one or more target agricultural fields; based on the application data, determining whether the one or more target agricultural fields are in compliance with the trial; receiving result data for the trial; based on the result data, computing a benefit value for the trial.

2. Example Agricultural Intelligence Computer System

2.1 Structural Overview

FIG. 1 illustrates an example computer system that is configured to perform the functions described herein, shown in a field environment with other apparatus with which the system may interoperate. In one embodiment, a user 102 owns, operates or possesses a field manager computing device 104 in a field location or associated with a field location such as a field intended for agricultural activities or a management location for one or more agricultural fields. The field manager computer device 104 is programmed or configured to provide field data 106 to an agricultural intelligence computer system 130 via one or more networks 109.

Examples of field data 106 include (a) identification data (for example, acreage, field name, field identifiers, geographic identifiers, boundary identifiers, crop identifiers, and any other suitable data that may be used to identify farm land, such as a common land unit (CLU), lot and block number, a parcel number, geographic coordinates and boundaries, Farm Serial Number (FSN), farm number, tract number, field number, section, township, and/or range), (b) harvest data (for example, crop type, crop variety, crop rotation, whether the crop is grown organically, harvest date, Actual Production History (APH), expected yield, yield, crop price, crop revenue, grain moisture, tillage practice, and previous growing season information), (c) soil data (for example, type, composition, pH, organic matter (OM), cation exchange capacity (CEC)), (d) planting data (for example, planting date, seed(s) type, relative maturity (RM) of planted seed(s), seed population), (e) fertilizer data (for example, nutrient type (Nitrogen, Phosphorous, Potassium), application type, application date, amount, source, method), (f) chemical application data (for example, pesticide, herbicide, fungicide, other substance or mixture of substances intended for use as a plant regulator, defoliant, or desiccant, application date, amount, source, method), (g) irrigation data (for example, application date, amount, source, method), (h) weather data (for example, precipitation, rainfall rate, predicted rainfall, water runoff rate region, temperature, wind, forecast, pressure, visibility, clouds, heat index, dew point, humidity, snow depth, air quality, sunrise, sunset), (i) imagery data (for example, imagery and light spectrum information from an agricultural apparatus sensor, camera, computer, smartphone, tablet, unmanned aerial vehicle, planes or satellite), (j) scouting observations (photos, videos, free form notes, voice recordings, voice transcriptions, weather conditions (temperature, precipitation (current and over time), soil moisture, crop growth stage, wind velocity, relative humidity, dew point, black layer)), and (k) soil, seed, crop phenology, pest and disease reporting, and predictions sources and databases.

A data server computer 108 is communicatively coupled to agricultural intelligence computer system 130 and is programmed or configured to send external data 110 to agricultural intelligence computer system 130 via the network(s) 109. The external data server computer 108 may be owned or operated by the same legal person or entity as the agricultural intelligence computer system 130, or by a different person or entity such as a government agency, non-governmental organization (NGO), and/or a private data service provider. Examples of external data include weather data, imagery data, soil data, or statistical data relating to crop yields, among others. External data 110 may consist of the same type of information as field data 106. In some embodiments, the external data 110 is provided by an external data server 108 owned by the same entity that owns and/or operates the agricultural intelligence computer system 130. For example, the agricultural intelligence computer system 130 may include a data server focused exclusively on a type of data that might otherwise be obtained from third party sources, such as weather data. In some embodiments, an external data server 108 may actually be incorporated within the system 130.

An agricultural apparatus 111 may have one or more remote sensors 112 fixed thereon, which sensors are communicatively coupled either directly or indirectly via agricultural apparatus 111 to the agricultural intelligence computer system 130 and are programmed or configured to send sensor data to agricultural intelligence computer system 130. Examples of agricultural apparatus 111 include tractors, combines, harvesters, planters, trucks, fertilizer equipment, aerial vehicles including unmanned aerial vehicles, and any other item of physical machinery or hardware, typically mobile machinery, and which may be used in tasks associated with agriculture. In some embodiments, a single unit of apparatus 111 may comprise a plurality of sensors 112 that are coupled locally in a network on the apparatus; controller area network (CAN) is example of such a network that can be installed in combines, harvesters, sprayers, and cultivators. Application controller 114 is communicatively coupled to agricultural intelligence computer system 130 via the network(s) 109 and is programmed or configured to receive one or more scripts that are used to control an operating parameter of an agricultural vehicle or implement from the agricultural intelligence computer system 130. For instance, a controller area network (CAN) bus interface may be used to enable communications from the agricultural intelligence computer system 130 to the agricultural apparatus 111, such as how the CLIMATE FIELDVIEW DRIVE, available from The Climate Corporation, San Francisco, California, is used. Sensor data may consist of the same type of information as field data 106. In some embodiments, remote sensors 112 may not be fixed to an agricultural apparatus 111 but may be remotely located in the field and may communicate with network 109.

The apparatus 111 may comprise a cab computer 115 that is programmed with a cab application, which may comprise a version or variant of the mobile application for device 104 that is further described in other sections herein. In an embodiment, cab computer 115 comprises a compact computer, often a tablet-sized computer or smartphone, with a graphical screen display, such as a color display, that is mounted within an operator's cab of the apparatus 111. Cab computer 115 may implement some or all of the operations and functions that are described further herein for the mobile computer device 104.

The network(s) 109 broadly represent any combination of one or more data communication networks including local area networks, wide area networks, internetworks or internets, using any of wireline or wireless links, including terrestrial or satellite links. The network(s) may be implemented by any medium or mechanism that provides for the exchange of data between the various elements of FIG. 1. The various elements of FIG. 1 may also have direct (wired or wireless) communications links. The sensors 112, controller 114, external data server computer 108, and other elements of the system each comprise an interface compatible with the network(s) 109 and are programmed or configured to use standardized protocols for communication across the networks such as TCP/IP, Bluetooth, CAN protocol and higher-layer protocols such as HTTP, TLS, and the like.

Agricultural intelligence computer system 130 is programmed or configured to receive field data 106 from field manager computing device 104, external data 110 from external data server computer 108, and sensor data from remote sensor 112. Agricultural intelligence computer system 130 may be further configured to host, use or execute one or more computer programs, other software elements, digitally programmed logic such as FPGAs or ASICs, or any combination thereof to perform translation and storage of data values, construction of digital models of one or more crops on one or more fields, generation of recommendations and notifications, and generation and sending of scripts to application controller 114, in the manner described further in other sections of this disclosure.

In an embodiment, agricultural intelligence computer system 130 is programmed with or comprises a communication layer 132, presentation layer 134, data management layer 140, hardware/virtualization layer 150, and model and field data repository 160. "Layer," in this context, refers to any combination of electronic digital interface circuits, microcontrollers, firmware such as drivers, and/or computer programs or other software elements.

Communication layer 132 may be programmed or configured to perform input/output interfacing functions including sending requests to field manager computing device 104, external data server computer 108, and remote sensor 112 for field data, external data, and sensor data respectively. Communication layer 132 may be programmed or configured to send the received data to model and field data repository 160 to be stored as field data 106.

Presentation layer 134 may be programmed or configured to generate a graphical user interface (GUI) to be displayed on field manager computing device 104, cab computer 115 or other computers that are coupled to the system 130 through the network 109. The GUI may comprise controls for inputting data to be sent to agricultural intelligence computer system 130, generating requests for models and/or recommendations, and/or displaying recommendations, notifications, models, and other field data.

Data management layer 140 may be programmed or configured to manage read operations and write operations involving the repository 160 and other functional elements of the system, including queries and result sets communicated between the functional elements of the system and the repository. Examples of data m60403-5052anagement layer 140 include JDBC, SQL server interface code, and/or HADOOP interface code, among others. Repository 160 may comprise a database. As used herein, the term "database" may refer to either a body of data, a relational database management system (RDBMS), or to both. As used herein, a database may comprise any collection of data including hierarchical databases, relational databases, flat file databases, object-relational databases, object oriented databases, distributed databases, and any other structured collection of records or data that is stored in a computer system.

Examples of RDBMS's include, but are not limited to including, ORACLE®, MYSQL, IBM® DB2, MICROSOFT® SQL SERVER, SYBASE®, and POSTGRESQL databases. However, any database may be used that enables the systems and methods described herein.

When field data 106 is not provided directly to the agricultural intelligence computer system via one or more agricultural machines or agricultural machine devices that interacts with the agricultural intelligence computer system, the user may be prompted via one or more user interfaces on the user device (served by the agricultural intelligence computer system) to input such information. In an example embodiment, the user may specify identification data by accessing a map on the user device (served by the agricultural intelligence computer system) and selecting specific CLUs that have been graphically shown on the map. In an alternative embodiment, the user 102 may specify identification data by accessing a map on the user device (served by the agricultural intelligence computer system 130) and drawing boundaries of the field over the map. Such CLU selection or map drawings represent geographic identifiers. In alternative embodiments, the user may specify identification data by accessing field identification data (provided as shape files or in a similar format) from the U. S. Department of Agriculture Farm Service Agency or other source via the user device and providing such field identification data to the agricultural intelligence computer system.

In an example embodiment, the agricultural intelligence computer system 130 is programmed to generate and cause displaying a graphical user interface comprising a data manager for data input. After one or more fields have been identified using the methods described above, the data manager may provide one or more graphical user interface widgets which when selected can identify changes to the field, soil, crops, tillage, or nutrient practices. The data manager may include a timeline view, a spreadsheet view, and/or one or more editable programs.

Figure 5:
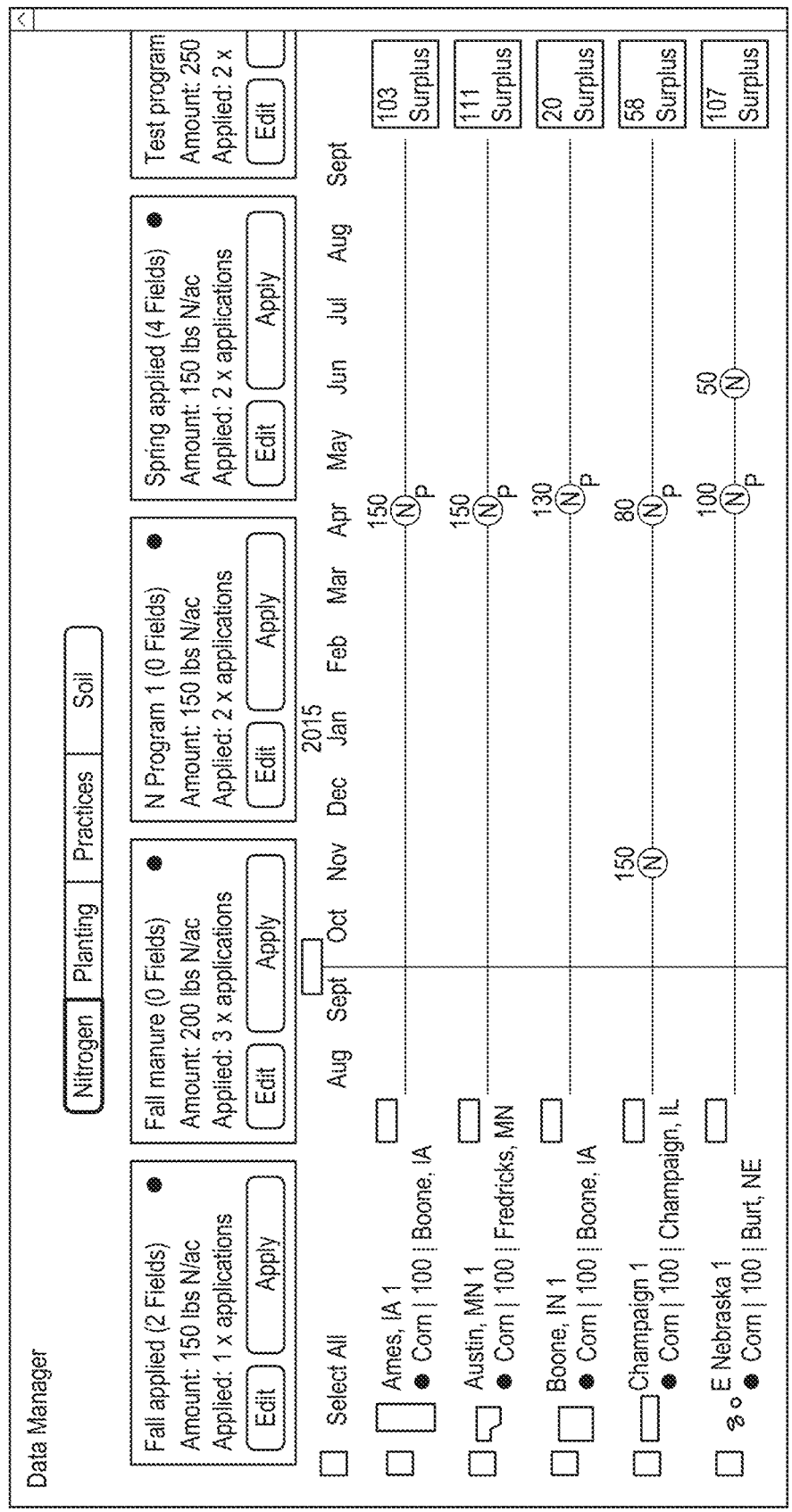
FIG. 5 depicts an example embodiment of a timeline view for data entry.

FIG. 5 depicts an example embodiment of a timeline view for data entry. Using the display depicted in FIG. 5, a user computer can input a selection of a particular field and a particular date for the addition of event. Events depicted at the top of the timeline may include Nitrogen, Planting, Practices, and Soil. To add a nitrogen application event, a user computer may provide input to select the nitrogen tab. The user computer may then select a location on the timeline for a particular field in order to indicate an application of nitrogen on the selected field. In response to receiving a selection of a location on the timeline for a particular field, the data manager may display a data entry overlay, allowing the user computer to input data pertaining to nitrogen applications, planting procedures, soil application, tillage procedures, irrigation practices, or other information relating to the particular field. For example, if a user computer selects a portion of the timeline and indicates an application of nitrogen, then the data entry overlay may include fields for inputting an amount of nitrogen applied, a date of application, a type of fertilizer used, and any other information related to the application of nitrogen.

In an embodiment, the data manager provides an interface for creating one or more programs. "Program," in this context, refers to a set of data pertaining to nitrogen applications, planting procedures, soil application, tillage procedures, irrigation practices, or other information that may be related to one or more fields, and that can be stored in digital data storage for reuse as a set in other operations. After a program has been created, it may be conceptually applied to one or more fields and references to the program may be stored in digital storage in association with data identifying the fields. Thus, instead of manually entering identical data relating to the same nitrogen applications for multiple different fields, a user computer may create a program that indicates a particular application of nitrogen and then apply the program to multiple different fields. For example, in the timeline view of FIG. 5, the top two timelines have the "Spring applied" program selected, which includes an application of 150 lbs N/ac in early April. The data manager may provide an interface for editing a program. In an embodiment, when a particular program is edited, each field that has selected the particular program is edited. For example, in FIG. 5, if the "Spring applied" program is edited to reduce the application of nitrogen to 130 lbs N/ac, the top two fields may be updated with a reduced application of nitrogen based on the edited program.

In an embodiment, in response to receiving edits to a field that has a program selected, the data manager removes the correspondence of the field to the selected program. For example, if a nitrogen application is added to the top field in FIG. 5, the interface may update to indicate that the "Spring applied" program is no longer being applied to the top field. While the nitrogen application in early April may remain, updates to the "Spring applied" program would not alter the April application of nitrogen.

FIG. 6 depicts an example embodiment of a spreadsheet view for data entry. Using the display depicted in FIG. 6, a user can create and edit information for one or more fields. The data manager may include spreadsheets for inputting information with respect to Nitrogen, Planting, Practices, and Soil as depicted in FIG. 6. To edit a particular entry, a user computer may select the particular entry in the spreadsheet and update the values. For example, FIG. 6 depicts an in-progress update to a target yield value for the second field. Additionally, a user computer may select one or more fields in order to apply one or more programs. In response to receiving a selection of a program for a particular field, the data manager may automatically complete the entries for the particular field based on the selected program. As with the timeline view, the data manager may update the entries for each field associated with a particular program in response to receiving an update to the program. Additionally, the data manager may remove the correspondence of the selected program to the field in response to receiving an edit to one of the entries for the field.

In an embodiment, model and field data is stored in model and field data repository 160. Model data comprises data models created for one or more fields. For example, a crop model may include a digitally constructed model of the development of a crop on the one or more fields. "Model," in this context, refers to an electronic digitally stored set of executable instructions and data values, associated with one another, which are capable of receiving and responding to a programmatic or other digital call, invocation, or request for resolution based upon specified input values, to yield one or more stored or calculated output values that can serve as the basis of computer-implemented recommendations, output data displays, or machine control, among other things. Persons of skill in the field find it convenient to express models using mathematical equations, but that form of expression does not confine the models disclosed herein to abstract concepts; instead, each model herein has a practical application in a computer in the form of stored executable instructions and data that implement the model using the computer. The model may include a model of past events on the one or more fields, a model of the current status of the one or more fields, and/or a model of predicted events on the one or more fields. Model and field data may be stored in data structures in memory, rows in a database table, in flat files or spreadsheets, or other forms of stored digital data.

In an embodiment, each of target identification instructions 135, trial design instructions 136, trial tracking instructions 137, and value association instructions 138 comprises a set of one or more pages of main memory, such as RAM, in the agricultural intelligence computer system 130 into which executable instructions have been loaded and which when executed cause the agricultural intelligence computing system to perform the functions or operations that are described herein with reference to those modules. For example, the target identification instructions 135 may comprise a set of pages in RAM that contain instructions which when executed cause performing the target identification functions that are described herein. The instructions may be in machine executable code in the instruction set of a CPU and may have been compiled based upon source code written in JAVA, C, C++, OBJECTIVE-C, or any other human-readable programming language or environment, alone or in combination with scripts in JAVASCRIPT, other scripting languages and other programming source text. The term "pages" is intended to refer broadly to any region within main memory and the specific terminology used in a system may vary depending on the memory architecture or processor architecture. In another embodiment, each of target identification instructions 135, trial design instructions 136, trial tracking instructions 137, and value association instructions 138 also may represent one or more files or projects of source code that are digitally stored in a mass storage device such as non-volatile RAM or disk storage, in the agricultural intelligence computer system 130 or a separate repository system, which when compiled or interpreted cause generating executable instructions which when executed cause the agricultural intelligence computing system to perform the functions or operations that are described herein with reference to those modules. In other words, the drawing figure may represent the manner in which programmers or software developers organize and arrange source code for later compilation into an executable, or interpretation into bytecode or the equivalent, for execution by the agricultural intelligence computer system 130.

Target identification instructions 135 comprise computer readable instructions which, when executed by one or more processors, cause agricultural intelligence computer system 130 to perform identification of one or more target fields that would benefit from implementing a trial and/or one or more field manager computing devices and/or field manager accounts associated with a field that would benefit from implementing a trial. Trial design instructions 136 comprise computer readable instructions which, when executed by one or more processors, cause agricultural intelligence computer system 130 to perform identification of one or more locations on an agricultural field for implementing a trial. Trial tracking instructions 137 comprise computer readable instructions which, when executed by one or more processors, cause agricultural intelligence computer system 130 to perform receiving field data and determining, based on the field data, whether an agricultural field is in compliance with one or more requirements of a trial. Value association instructions 138 comprise computer readable instructions which, when executed by one or more processors, cause agricultural intelligence computer system 130 to perform associating a value with the results of one or more trials.

Figure 4:
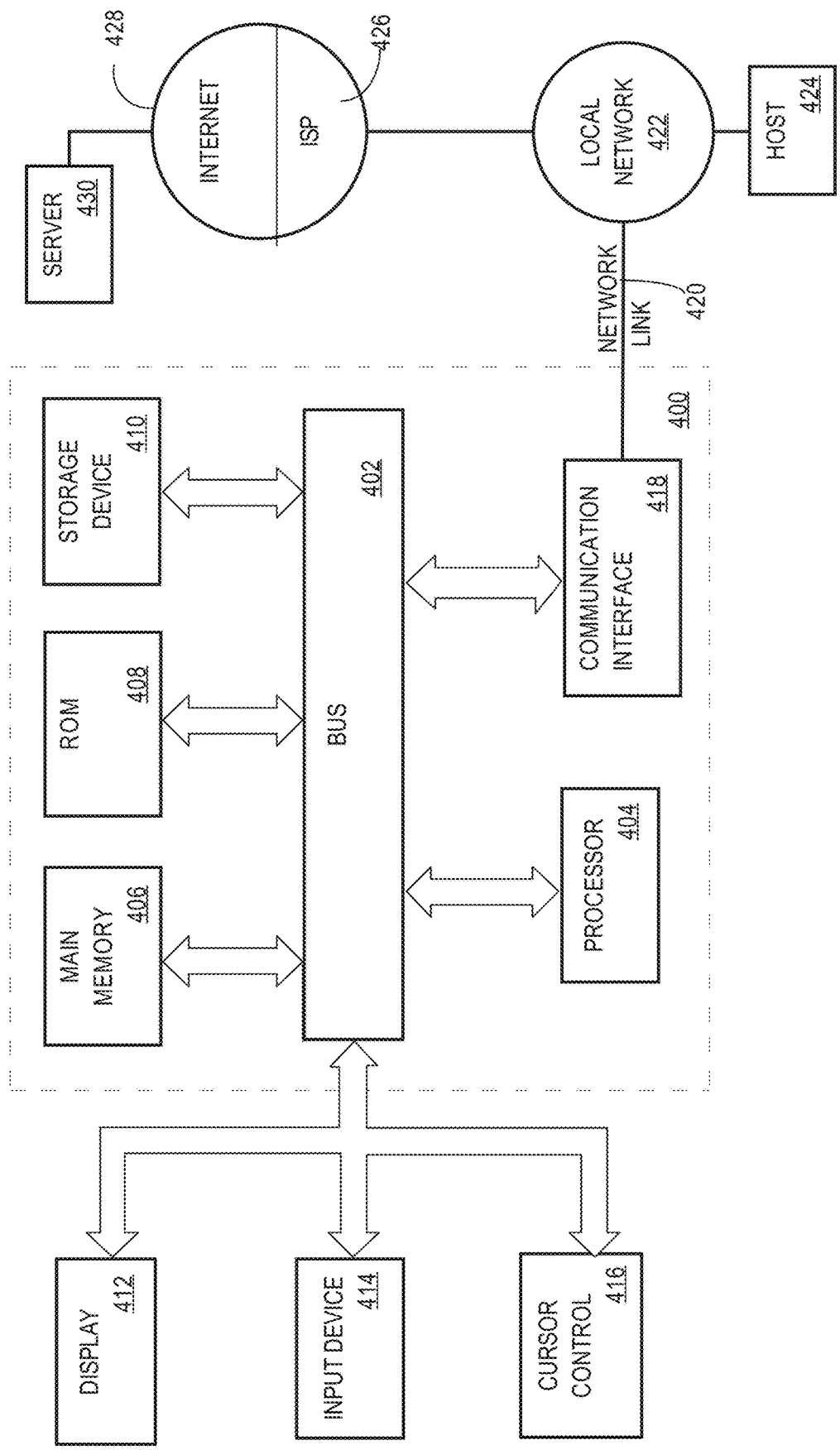
FIG. 4 is a block diagram that illustrates a computer system upon which an embodiment of the invention may be implemented.

Hardware/virtualization layer 150 comprises one or more central processing units (CPUs), memory controllers, and other devices, components, or elements of a computer system such as volatile or non-volatile memory, non-volatile storage such as disk, and I/O devices or interfaces as illustrated and described, for example, in connection with FIG. 4. The layer 150 also may comprise programmed instructions that are configured to support virtualization, containerization, or other technologies.

For purposes of illustrating a clear example, FIG. 1 shows a limited number of instances of certain functional elements. However, in other embodiments, there may be any number of such elements. For example, embodiments may use thousands or millions of different mobile computing devices 104 associated with different users. Further, the system 130 and/or external data server computer 108 may be implemented using two or more processors, cores, clusters, or instances of physical machines or virtual machines, configured in a discrete location or co-located with other elements in a datacenter, shared computing facility or cloud computing facility.

2.2. Application Program Overview

In an embodiment, the implementation of the functions described herein using one or more computer programs or other software elements that are loaded into and executed using one or more general-purpose computers will cause the general-purpose computers to be configured as a particular machine or as a computer that is specially adapted to perform the functions described herein. Further, each of the flow diagrams that are described further herein may serve, alone or in combination with the descriptions of processes and functions in prose herein, as algorithms, plans or directions that may be used to program a computer or logic to implement the functions that are described. In other words, all the prose text herein, and all the drawing figures, together are intended to provide disclosure of algorithms, plans or directions that are sufficient to permit a skilled person to program a computer to perform the functions that are described herein, in combination with the skill and knowledge of such a person given the level of skill that is appropriate for inventions and disclosures of this type.

In an embodiment, user 102 interacts with agricultural intelligence computer system 130 using field manager computing device 104 configured with an operating system and one or more application programs or apps; the field manager computing device 104 also may interoperate with the agricultural intelligence computer system independently and automatically under program control or logical control and direct user interaction is not always required. Field manager computing device 104 broadly represents one or more of a smart phone, PDA, tablet computing device, laptop computer, desktop computer, workstation, or any other computing device capable of transmitting and receiving information and performing the functions described herein. Field manager computing device 104 may communicate via a network using a mobile application stored on field manager computing device 104, and in some embodiments, the device may be coupled using a cable 113 or connector to the sensor 112 and/or controller 114. A particular user 102 may own, operate or possess and use, in connection with system 130, more than one field manager computing device 104 at a time.

The mobile application may provide client-side functionality, via the network to one or more mobile computing devices. In an example embodiment, field manager computing device 104 may access the mobile application via a web browser or a local client application or app. Field manager computing device 104 may transmit data to, and receive data from, one or more front-end servers, using web-based protocols or formats such as HTTP, XML and/or JSON, or app-specific protocols. In an example embodiment, the data may take the form of requests and user information input, such as field data, into the mobile computing device. In some embodiments, the mobile application interacts with location tracking hardware and software on field manager computing device 104 which determines the location of field manager computing device 104 using standard tracking techniques such as multilateration of radio signals, the global positioning system (GPS), WiFi positioning systems, or other methods of mobile positioning. In some cases, location data or other data associated with the device 104, user 102, and/or user account(s) may be obtained by queries to an operating system of the device or by requesting an app on the device to obtain data from the operating system.

In an embodiment, field manager computing device 104 sends field data 106 to agricultural intelligence computer system 130 comprising or including, but not limited to, data values representing one or more of: a geographical location of the one or more fields, tillage information for the one or more fields, crops planted in the one or more fields, and soil data extracted from the one or more fields. Field manager computing device 104 may send field data 106 in response to user input from user 102 specifying the data values for the one or more fields. Additionally, field manager computing device 104 may automatically send field data 106 when one or more of the data values becomes available to field manager computing device 104. For example, field manager computing device 104 may be communicatively coupled to remote sensor 112 and/or application controller 114 which include an irrigation sensor and/or irrigation controller. In response to receiving data indicating that application controller 114 released water onto the one or more fields, field manager computing device 104 may send field data 106 to agricultural intelligence computer system 130 indicating that water was released on the one or more fields. Field data 106 identified in this disclosure may be input and communicated using electronic digital data that is communicated between computing devices using parameterized URLs over HTTP, or another suitable communication or messaging protocol.

A commercial example of the mobile application is CLIMATE FIELDVIEW, commercially available from The Climate Corporation, San Francisco, California. The CLIMATE FIELDVIEW application, or other applications, may be modified, extended, or adapted to include features, functions, and programming that have not been disclosed earlier than the filing date of this disclosure. In one embodiment, the mobile application comprises an integrated software platform that allows a grower to make fact-based decisions for their operation because it combines historical data about the grower's fields with any other data that the grower wishes to compare. The combinations and comparisons may be performed in real time and are based upon scientific models that provide potential scenarios to permit the grower to make better, more informed decisions.

FIG. 2 illustrates two views of an example logical organization of sets of instructions in main memory when an example mobile application is loaded for execution. In FIG. 2, each named element represents a region of one or more pages of RAM or other main memory, or one or more blocks of disk storage or other non-volatile storage, and the programmed instructions within those regions. In one embodiment, in view (a), a mobile computer application 200 comprises account-fields-data ingestion-sharing instructions 202, overview and alert instructions 204, digital map book instructions 206, seeds and planting instructions 208, nitrogen instructions 210, weather instructions 212, field health instructions 214, and performance instructions 216.

In one embodiment, a mobile computer application 200 comprises account, fields, data ingestion, sharing instructions 202 which are programmed to receive, translate, and ingest field data from third party systems via manual upload or APIs. Data types may include field boundaries, yield maps, as-planted maps, soil test results, as-applied maps, and/or management zones, among others. Data formats may include shape files, native data formats of third parties, and/or farm management information system (FMIS) exports, among others. Receiving data may occur via manual upload, e-mail with attachment, external APIs that push data to the mobile application, or instructions that call APIs of external systems to pull data into the mobile application. In one embodiment, mobile computer application 200 comprises a data inbox. In response to receiving a selection of the data inbox, the mobile computer application 200 may display a graphical user interface for manually uploading data files and importing uploaded files to a data manager.

In one embodiment, digital map book instructions 206 comprise field map data layers stored in device memory and are programmed with data visualization tools and geospatial field notes. This provides growers with convenient information close at hand for reference, logging and visual insights into field performance. In one embodiment, overview and alert instructions 204 are programmed to provide an operation-wide view of what is important to the grower, and timely recommendations to take action or focus on particular issues. This permits the grower to focus time on what needs attention, to save time and preserve yield throughout the season. In one embodiment, seeds and planting instructions 208 are programmed to provide tools for seed selection, hybrid placement, and script creation, including variable rate (VR) script creation, based upon scientific models and empirical data. This enables growers to maximize yield or return on investment through optimized seed purchase, placement and population.

In one embodiment, script generation instructions 205 are programmed to provide an interface for generating scripts, including variable rate (VR) fertility scripts. The interface enables growers to create scripts for field implements, such as nutrient applications, planting, and irrigation. For example, a planting script interface may comprise tools for identifying a type of seed for planting. Upon receiving a selection of the seed type, mobile computer application 200 may display one or more fields broken into management zones, such as the field map data layers created as part of digital map book instructions 206. In one embodiment, the management zones comprise soil zones along with a panel identifying each soil zone and a soil name, texture, drainage for each zone, or other field data. Mobile computer application 200 may also display tools for editing or creating such, such as graphical tools for drawing management zones, such as soil zones, over a map of one or more fields. Planting procedures may be applied to all management zones or different planting procedures may be applied to different subsets of management zones. When a script is created, mobile computer application 200 may make the script available for download in a format readable by an application controller, such as an archived or compressed format. Additionally, and/or alternatively, a script may be sent directly to cab computer 115 from mobile computer application 200 and/or uploaded to one or more data servers and stored for further use.

In one embodiment, nitrogen instructions 210 are programmed to provide tools to inform nitrogen decisions by visualizing the availability of nitrogen to crops. This enables growers to maximize yield or return on investment through optimized nitrogen application during the season. Example programmed functions include displaying images such as SSURGO images to enable drawing of fertilizer application zones and/or images generated from subfield soil data, such as data obtained from sensors, at a high spatial resolution (as fine as millimeters or smaller depending on sensor proximity and resolution); upload of existing grower-defined zones; providing a graph of plant nutrient availability and/or a map to enable tuning application(s) of nitrogen across multiple zones; output of scripts to drive machinery; tools for mass data entry and adjustment; and/or maps for data visualization, among others. "Mass data entry," in this context, may mean entering data once and then applying the same data to multiple fields and/or zones that have been defined in the system; example data may include nitrogen application data that is the same for many fields and/or zones of the same grower, but such mass data entry applies to the entry of any type of field data into the mobile computer application 200. For example, nitrogen instructions 210 may be programmed to accept definitions of nitrogen application and practices programs and to accept user input specifying to apply those programs across multiple fields. "Nitrogen application programs," in this context, refers to stored, named sets of data that associates: a name, color code or other identifier, one or more dates of application, types of material or product for each of the dates and amounts, method of application or incorporation such as injected or broadcast, and/or amounts or rates of application for each of the dates, crop or hybrid that is the subject of the application, among others. "Nitrogen practices programs," in this context, refer to stored, named sets of data that associates: a practices name; a previous crop; a tillage system; a date of primarily tillage; one or more previous tillage systems that were used; one or more indicators of application type, such as manure, that were used. Nitrogen instructions 210 also may be programmed to generate and cause displaying a nitrogen graph, which indicates projections of plant use of the specified nitrogen and whether a surplus or shortfall is predicted; in some embodiments, different color indicators may signal a magnitude of surplus or magnitude of shortfall. In one embodiment, a nitrogen graph comprises a graphical display in a computer display device comprising a plurality of rows, each row associated with and identifying a field; data specifying what crop is planted in the field, the field size, the field location, and a graphic representation of the field perimeter; in each row, a timeline by month with graphic indicators specifying each nitrogen application and amount at points correlated to month names; and numeric and/or colored indicators of surplus or shortfall, in which color indicates magnitude.

In one embodiment, the nitrogen graph may include one or more user input features, such as dials or slider bars, to dynamically change the nitrogen planting and practices programs so that a user may optimize his nitrogen graph. The user may then use his optimized nitrogen graph and the related nitrogen planting and practices programs to implement one or more scripts, including variable rate (VR) fertility scripts. Nitrogen instructions 210 also may be programmed to generate and cause displaying a nitrogen map, which indicates projections of plant use of the specified nitrogen and whether a surplus or shortfall is predicted; in some embodiments, different color indicators may signal a magnitude of surplus or magnitude of shortfall. The nitrogen map may display projections of plant use of the specified nitrogen and whether a surplus or shortfall is predicted for different times in the past and the future (such as daily, weekly, monthly or yearly) using numeric and/or colored indicators of surplus or shortfall, in which color indicates magnitude. In one embodiment, the nitrogen map may include one or more user input features, such as dials or slider bars, to dynamically change the nitrogen planting and practices programs so that a user may optimize his nitrogen map, such as to obtain a preferred amount of surplus to shortfall. The user may then use his optimized nitrogen map and the related nitrogen planting and practices programs to implement one or more scripts, including variable rate (VR) fertility scripts. In other embodiments, similar instructions to the nitrogen instructions 210 could be used for application of other nutrients (such as phosphorus and potassium), application of pesticide, and irrigation programs.

In one embodiment, weather instructions 212 are programmed to provide field-specific recent weather data and forecasted weather information. This enables growers to save time and have an efficient integrated display with respect to daily operational decisions.

In one embodiment, field health instructions 214 are programmed to provide timely remote sensing images highlighting in-season crop variation and potential concerns. Example programmed functions include cloud checking, to identify possible clouds or cloud shadows; determining nitrogen indices based on field images; graphical visualization of scouting layers, including, for example, those related to field health, and viewing and/or sharing of scouting notes; and/or downloading satellite images from multiple sources and prioritizing the images for the grower, among others.

In one embodiment, performance instructions 216 are programmed to provide reports, analysis, and insight tools using on-farm data for evaluation, insights and decisions. This enables the grower to seek improved outcomes for the next year through fact-based conclusions about why return on investment was at prior levels, and insight into yield-limiting factors. The performance instructions 216 may be programmed to communicate via the network(s) 109 to back-end analytics programs executed at agricultural intelligence computer system 130 and/or external data server computer 108 and configured to analyze metrics such as yield, yield differential, hybrid, population, SSURGO zone, soil test properties, or elevation, among others. Programmed reports and analysis may include yield variability analysis, treatment effect estimation, benchmarking of yield and other metrics against other growers based on anonymized data collected from many growers, or data for seeds and planting, among others.

Applications having instructions configured in this way may be implemented for different computing device platforms while retaining the same general user interface appearance. For example, the mobile application may be programmed for execution on tablets, smartphones, or server computers that are accessed using browsers at client computers. Further, the mobile application as configured for tablet computers or smartphones may provide a full app experience or a cab app experience that is suitable for the display and processing capabilities of cab computer 115. For example, referring now to view (b) of FIG. 2, in one embodiment a cab computer application 220 may comprise maps-cab instructions 222, remote view instructions 224, data collect and transfer instructions 226, machine alerts instructions 228, script transfer instructions 230, and scouting-cab instructions 232. The code base for the instructions of view (b) may be the same as for view (a) and executables implementing the code may be programmed to detect the type of platform on which they are executing and to expose, through a graphical user interface, only those functions that are appropriate to a cab platform or full platform. This approach enables the system to recognize the distinctly different user experience that is appropriate for an in-cab environment and the different technology environment of the cab. The maps-cab instructions 222 may be programmed to provide map views of fields, farms or regions that are useful in directing machine operation. The remote view instructions 224 may be programmed to turn on, manage, and provide views of machine activity in real-time or near real-time to other computing devices connected to the system 130 via wireless networks, wired connectors or adapters, and the like. The data collect and transfer instructions 226 may be programmed to turn on, manage, and provide transfer of data collected at sensors and controllers to the system 130 via wireless networks, wired connectors or adapters, and the like. The machine alerts instructions 228 may be programmed to detect issues with operations of the machine or tools that are associated with the cab and generate operator alerts. The script transfer instructions 230 may be configured to transfer in scripts of instructions that are configured to direct machine operations or the collection of data. The scouting-cab instructions 232 may be programmed to display location-based alerts and information received from the system 130 based on the location of the field manager computing device 104, agricultural apparatus 111, or sensors 112 in the field and ingest, manage, and provide transfer of location-based scouting observations to the system 130 based on the location of the agricultural apparatus 111 or sensors 112 in the field.

2.3. Data Ingest to the Computer System

In an embodiment, external data server computer 108 stores external data 110, including soil data representing soil composition for the one or more fields and weather data representing temperature and precipitation on the one or more fields. The weather data may include past and present weather data as well as forecasts for future weather data. In an embodiment, external data server computer 108 comprises a plurality of servers hosted by different entities. For example, a first server may contain soil composition data while a second server may include weather data. Additionally, soil composition data may be stored in multiple servers. For example, one server may store data representing percentage of sand, silt, and clay in the soil while a second server may store data representing percentage of organic matter (OM) in the soil.

In an embodiment, remote sensor 112 comprises one or more sensors that are programmed or configured to produce one or more observations. Remote sensor 112 may be aerial sensors, such as satellites, vehicle sensors, planting equipment sensors, tillage sensors, fertilizer or insecticide application sensors, harvester sensors, and any other implement capable of receiving data from the one or more fields. In an embodiment, application controller 114 is programmed or configured to receive instructions from agricultural intelligence computer system 130. Application controller 114 may also be programmed or configured to control an operating parameter of an agricultural vehicle or implement. For example, an application controller may be programmed or configured to control an operating parameter of a vehicle, such as a tractor, planting equipment, tillage equipment, fertilizer or insecticide equipment, harvester equipment, or other farm implements such as a water valve. Other embodiments may use any combination of sensors and controllers, of which the following are merely selected examples.

The system 130 may obtain or ingest data under user 102 control, on a mass basis from a large number of growers who have contributed data to a shared database system. This form of obtaining data may be termed "manual data ingest" as one or more user-controlled computer operations are requested or triggered to obtain data for use by the system 130. As an example, the CLIMATE FIELDVIEW application, commercially available from The Climate Corporation, San Francisco, California, may be operated to export data to system 130 for storing in the repository 160.

For example, seed monitor systems can both control planter apparatus components and obtain planting data, including signals from seed sensors via a signal harness that comprises a CAN backbone and point-to-point connections for registration and/or diagnostics. Seed monitor systems can be programmed or configured to display seed spacing, population and other information to the user via the cab computer 115 or other devices within the system 130. Examples are disclosed in U.S. Pat. No. 8,738,243 and US Pat. Pub. 20150094916, and the present disclosure assumes knowledge of those other patent disclosures.

Likewise, yield monitor systems may contain yield sensors for harvester apparatus that send yield measurement data to the cab computer 115 or other devices within the system 130. Yield monitor systems may utilize one or more remote sensors 112 to obtain grain moisture measurements in a combine or other harvester and transmit these measurements to the user via the cab computer 115 or other devices within the system 130.

In an embodiment, examples of sensors 112 that may be used with any moving vehicle or apparatus of the type described elsewhere herein include kinematic sensors and position sensors. Kinematic sensors may comprise any of speed sensors such as radar or wheel speed sensors, accelerometers, or gyros. Position sensors may comprise GPS receivers or transceivers, or WiFi-based position or mapping apps that are programmed to determine location based upon nearby WiFi hotspots, among others.

In an embodiment, examples of sensors 112 that may be used with tractors or other moving vehicles include engine speed sensors, fuel consumption sensors, area counters or distance counters that interact with GPS or radar signals, PTO (power take-off) speed sensors, tractor hydraulics sensors configured to detect hydraulics parameters such as pressure or flow, and/or and hydraulic pump speed, wheel speed sensors or wheel slippage sensors. In an embodiment, examples of controllers 114 that may be used with tractors include hydraulic directional controllers, pressure controllers, and/or flow controllers; hydraulic pump speed controllers; speed controllers or governors; hitch position controllers; or wheel position controllers provide automatic steering.

In an embodiment, examples of sensors 112 that may be used with seed planting equipment such as planters, drills, or air seeders include seed sensors, which may be optical, electromagnetic, or impact sensors; downforce sensors such as load pins, load cells, pressure sensors; soil property sensors such as reflectivity sensors, moisture sensors, electrical conductivity sensors, optical residue sensors, or temperature sensors; component operating criteria sensors such as planting depth sensors, downforce cylinder pressure sensors, seed disc speed sensors, seed drive motor encoders, seed conveyor system speed sensors, or vacuum level sensors; or pesticide application sensors such as optical or other electromagnetic sensors, or impact sensors. In an embodiment, examples of controllers 114 that may be used with such seed planting equipment include: toolbar fold controllers, such as controllers for valves associated with hydraulic cylinders; downforce controllers, such as controllers for valves associated with pneumatic cylinders, airbags, or hydraulic cylinders, and programmed for applying downforce to individual row units or an entire planter frame; planting depth controllers, such as linear actuators; metering controllers, such as electric seed meter drive motors, hydraulic seed meter drive motors, or swath control clutches; hybrid selection controllers, such as seed meter drive motors, or other actuators programmed for selectively allowing or preventing seed or an air-seed mixture from delivering seed to or from seed meters or central bulk hoppers; metering controllers, such as electric seed meter drive motors, or hydraulic seed meter drive motors; seed conveyor system controllers, such as controllers for a belt seed delivery conveyor motor; marker controllers, such as a controller for a pneumatic or hydraulic actuator; or pesticide application rate controllers, such as metering drive controllers, orifice size or position controllers.

In an embodiment, examples of sensors 112 that may be used with tillage equipment include position sensors for tools such as shanks or discs; tool position sensors for such tools that are configured to detect depth, gang angle, or lateral spacing; downforce sensors; or draft force sensors. In an embodiment, examples of controllers 114 that may be used with tillage equipment include downforce controllers or tool position controllers, such as controllers configured to control tool depth, gang angle, or lateral spacing.

In an embodiment, examples of sensors 112 that may be used in relation to apparatus for applying fertilizer, insecticide, fungicide and the like, such as on-planter starter fertilizer systems, subsoil fertilizer applicators, or fertilizer sprayers, include: fluid system criteria sensors, such as flow sensors or pressure sensors; sensors indicating which spray head valves or fluid line valves are open; sensors associated with tanks, such as fill level sensors; sectional or system-wide supply line sensors, or row-specific supply line sensors; or kinematic sensors such as accelerometers disposed on sprayer booms. In an embodiment, examples of controllers 114 that may be used with such apparatus include pump speed controllers; valve controllers that are programmed to control pressure, flow, direction, PWM and the like; or position actuators, such as for boom height, subsoiler depth, or boom position.

In an embodiment, examples of sensors 112 that may be used with harvesters include yield monitors, such as impact plate strain gauges or position sensors, capacitive flow sensors, load sensors, weight sensors, or torque sensors associated with elevators or augers, or optical or other electromagnetic grain height sensors; grain moisture sensors, such as capacitive sensors; grain loss sensors, including impact, optical, or capacitive sensors; header operating criteria sensors such as header height, header type, deck plate gap, feeder speed, and reel speed sensors; separator operating criteria sensors, such as concave clearance, rotor speed, shoe clearance, or chaffer clearance sensors; auger sensors for position, operation, or speed; or engine speed sensors. In an embodiment, examples of controllers 114 that may be used with harvesters include header operating criteria controllers for elements such as header height, header type, deck plate gap, feeder speed, or reel speed; separator operating criteria controllers for features such as concave clearance, rotor speed, shoe clearance, or chaffer clearance; or controllers for auger position, operation, or speed.

In an embodiment, examples of sensors 112 that may be used with grain carts include weight sensors, or sensors for auger position, operation, or speed. In an embodiment, examples of controllers 114 that may be used with grain carts include controllers for auger position, operation, or speed.

In an embodiment, examples of sensors 112 and controllers 114 may be installed in unmanned aerial vehicle (UAV) apparatus or "drones." Such sensors may include cameras with detectors effective for any range of the electromagnetic spectrum including visible light, infrared, ultraviolet, near-infrared (NIR), and the like; accelerometers; altimeters; temperature sensors; humidity sensors; pitot tube sensors or other airspeed or wind velocity sensors; battery life sensors; or radar emitters and reflected radar energy detection apparatus; other electromagnetic radiation emitters and reflected electromagnetic radiation detection apparatus. Such controllers may include guidance or motor control apparatus, control surface controllers, camera controllers, or controllers programmed to turn on, operate, obtain data from, manage and configure any of the foregoing sensors. Examples are disclosed in U.S. patent application Ser. No. 14/831,165 and the present disclosure assumes knowledge of that other patent disclosure.

In an embodiment, sensors 112 and controllers 114 may be affixed to soil sampling and measurement apparatus that is configured or programmed to sample soil and perform soil chemistry tests, soil moisture tests, and other tests pertaining to soil. For example, the apparatus disclosed in U.S. Pat. Nos. 8,767,194 and 8,712,148 may be used, and the present disclosure assumes knowledge of those patent disclosures.

In an embodiment, sensors 112 and controllers 114 may comprise weather devices for monitoring weather conditions of fields. For example, the apparatus disclosed in U.S. Provisional Application No. 62/154,207, filed on Apr. 29, 2015, U.S. Provisional Application No. 62/175,160, filed on Jun. 12, 2015, U.S. Provisional Application No. 62/198,060, filed on Jul. 28, 2015, and U.S. Provisional Application No. 62/220,852, filed on Sep. 18, 2015, may be used, and the present disclosure assumes knowledge of those patent disclosures.

2.4. Process Overview-Agronomic Model Training

In an embodiment, the agricultural intelligence computer system 130 is programmed or configured to create an agronomic model. In this context, an agronomic model is a data structure in memory of the agricultural intelligence computer system 130 that comprises field data 106, such as identification data and harvest data for one or more fields. The agronomic model may also comprise calculated agronomic properties which describe either conditions which may affect the growth of one or more crops on a field, or properties of the one or more crops, or both. Additionally, an agronomic model may comprise recommendations based on agronomic factors such as crop recommendations, irrigation recommendations, planting recommendations, fertilizer recommendations, fungicide recommendations, pesticide recommendations, harvesting recommendations and other crop management recommendations. The agronomic factors may also be used to estimate one or more crop related results, such as agronomic yield. The agronomic yield of a crop is an estimate of quantity of the crop that is produced, or in some examples the revenue or profit obtained from the produced crop.

In an embodiment, the agricultural intelligence computer system 130 may use a preconfigured agronomic model to calculate agronomic properties related to currently received location and crop information for one or more fields. The preconfigured agronomic model is based upon previously processed field data, including but not limited to, identification data, harvest data, fertilizer data, and weather data. The preconfigured agronomic model may have been cross validated to ensure accuracy of the model. Cross validation may include comparison to ground truthing that compares predicted results with actual results on a field, such as a comparison of precipitation estimate with a rain gauge or sensor providing weather data at the same or nearby location or an estimate of nitrogen content with a soil sample measurement.

Figure 3:
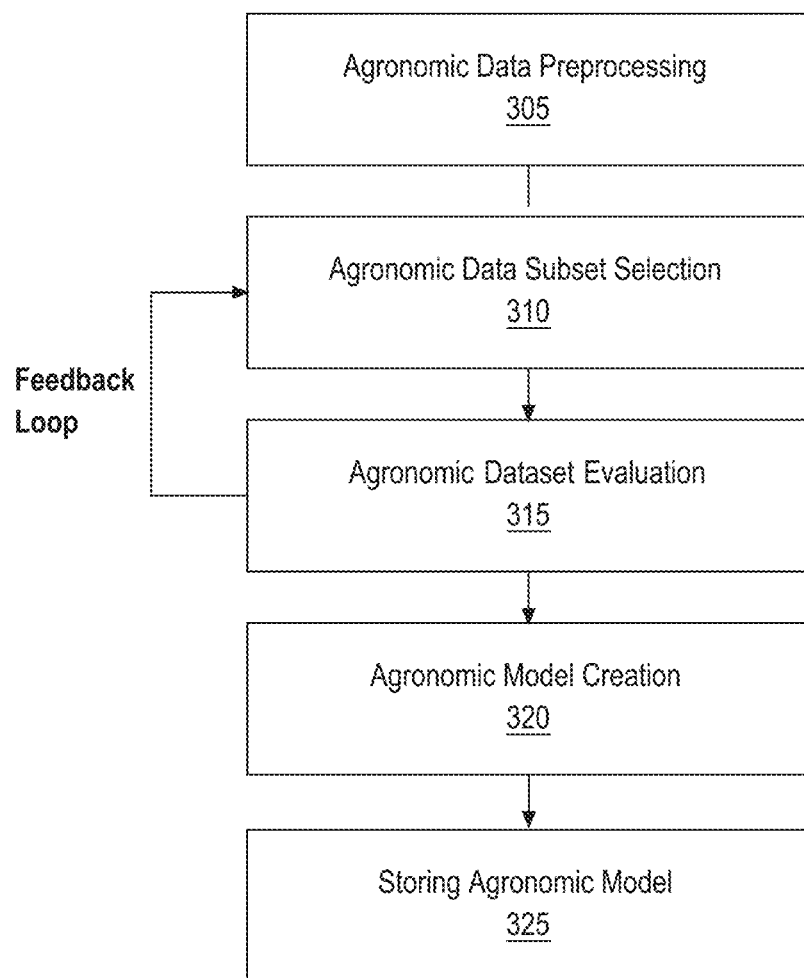
FIG. 3 illustrates a programmed process by which the agricultural intelligence computer system generates one or more preconfigured agronomic models using agronomic data provided by one or more data sources.

FIG. 3 illustrates a programmed process by which the agricultural intelligence computer system generates one or more preconfigured agronomic models using field data provided by one or more data sources. FIG. 3 may serve as an algorithm or instructions for programming the functional elements of the agricultural intelligence computer system 130 to perform the operations that are now described.

At block 305, the agricultural intelligence computer system 130 is configured or programmed to implement agronomic data preprocessing of field data received from one or more data sources. The field data received from one or more data sources may be preprocessed for the purpose of removing noise, distorting effects, and confounding factors within the agronomic data including measured outliers that could adversely affect received field data values. Embodiments of agronomic data preprocessing may include, but are not limited to, removing data values commonly associated with outlier data values, specific measured data points that are known to unnecessarily skew other data values, data smoothing, aggregation, or sampling techniques used to remove or reduce additive or multiplicative effects from noise, and other filtering or data derivation techniques used to provide clear distinctions between positive and negative data inputs.

At block 310, the agricultural intelligence computer system 130 is configured or programmed to perform data subset selection using the preprocessed field data in order to identify datasets useful for initial agronomic model generation. The agricultural intelligence computer system 130 may implement data subset selection techniques including, but not limited to, a genetic algorithm method, an all subset models method, a sequential search method, a stepwise regression method, a particle swarm optimization method, and an ant colony optimization method. For example, a genetic algorithm selection technique uses an adaptive heuristic search algorithm, based on evolutionary principles of natural selection and genetics, to determine and evaluate datasets within the preprocessed agronomic data.

At block 315, the agricultural intelligence computer system 130 is configured or programmed to implement field dataset evaluation. In an embodiment, a specific field dataset is evaluated by creating an agronomic model and using specific quality thresholds for the created agronomic model. Agronomic models may be compared and/or validated using one or more comparison techniques, such as, but not limited to, root mean square error with leave-one-out cross validation (RMSECV), mean absolute error, and mean percentage error. For example, RMSECV can cross validate agronomic models by comparing predicted agronomic property values created by the agronomic model against historical agronomic property values collected and analyzed. In an embodiment, the agronomic dataset evaluation logic is used as a feedback loop where agronomic datasets that do not meet configured quality thresholds are used during future data subset selection steps (block 310).

At block 320, the agricultural intelligence computer system 130 is configured or programmed to implement agronomic model creation based upon the cross validated agronomic datasets. In an embodiment, agronomic model creation may implement multivariate regression techniques to create preconfigured agronomic data models.

At block 325, the agricultural intelligence computer system 130 is configured or programmed to store the preconfigured agronomic data models for future field data evaluation.

2.5. Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

For example, FIG. 4 is a block diagram that illustrates a computer system 400 upon which an embodiment of the invention may be implemented. Computer system 400 includes a bus 402 or other communication mechanism for communicating information, and a hardware processor 404 coupled with bus 402 for processing information. Hardware processor 404 may be, for example, a general purpose microprocessor.

Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk, optical disk, or solid-state drive is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

Computer system 400 may implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 410. Volatile media includes dynamic memory, such as main memory 406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 402. Transmission media can also take the form of acoustic or light waves, such as those generated during radio-wave and infrared data communications.

Various forms of media may be involved in carrying one or more sequences of one or more instructions to processor 404 for execution. For example, the instructions may initially be carried on a magnetic disk or solid-state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infrared signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

3. Functional Overview

Systems and methods for implementing trials in one or more fields are described herein. As used herein, a trial refers to performing one or more different agricultural activities in a portion of an agricultural field in order to identify a benefit or detriment of performing the one or more different agricultural activities. As an example, a subfield area may be selected in an agricultural field i to implement a fungicide trial. Within the subfield area, the crops may receive an application of fungicide while the rest of the field and/or a different subfield area on the field does not receive an application of fungicide. Alternatively, the rest of the field may receive the application of fungicide while the crops within the subfield area do not. The subfield areas of the field where the one or more different agricultural activities are performed are referred to herein as test locations. In some embodiments, subfield areas that do not include the different agricultural activities can also be assigned and referred to as test locations.

Trials may be performed for testing the efficacy of new products, different management practices, different crops, or any combination thereof. For example, if a field usually does not receive fungicide, a trial may be designed wherein crops within a selected portion of the field receive fungicide at one or more times during the development of the crop. As another example, if a field usually is conventionally tilled, a trial may be designed wherein a selected portion of the field is not tilled. Thus, trials may be implemented for determining whether to follow management practice recommendations instead of being constrained to testing the efficacy of a particular product. Additionally or alternatively, trials may be designed to compare two different types of products, planting rates, equipment, and/or other management practices.

Trials may be constrained by one or more rules. A trial may require one or more testing locations to be of a particular size and/or placed in a particular location. For example, the trial may require one or more testing locations to be placed in an area of the field with comparable conditions to the rest of the field. A testing location, as used herein, refers to an area of an agronomic field that receives one or more different treatments from surrounding areas. Thus, a testing location may refer to any shape of land on an agronomic field. Additionally or alternatively, the trial may require one or more testing locations to be placed in an area of the field with conditions differing from the rest of the field and/or areas of the field spanning different types of conditions. The trial may require one or more different management practices to be undertaken in one or more testing locations. For example, a trial may require a particular seeding rate as part of a test for planting a different type of hybrid seed.

Figure 7:
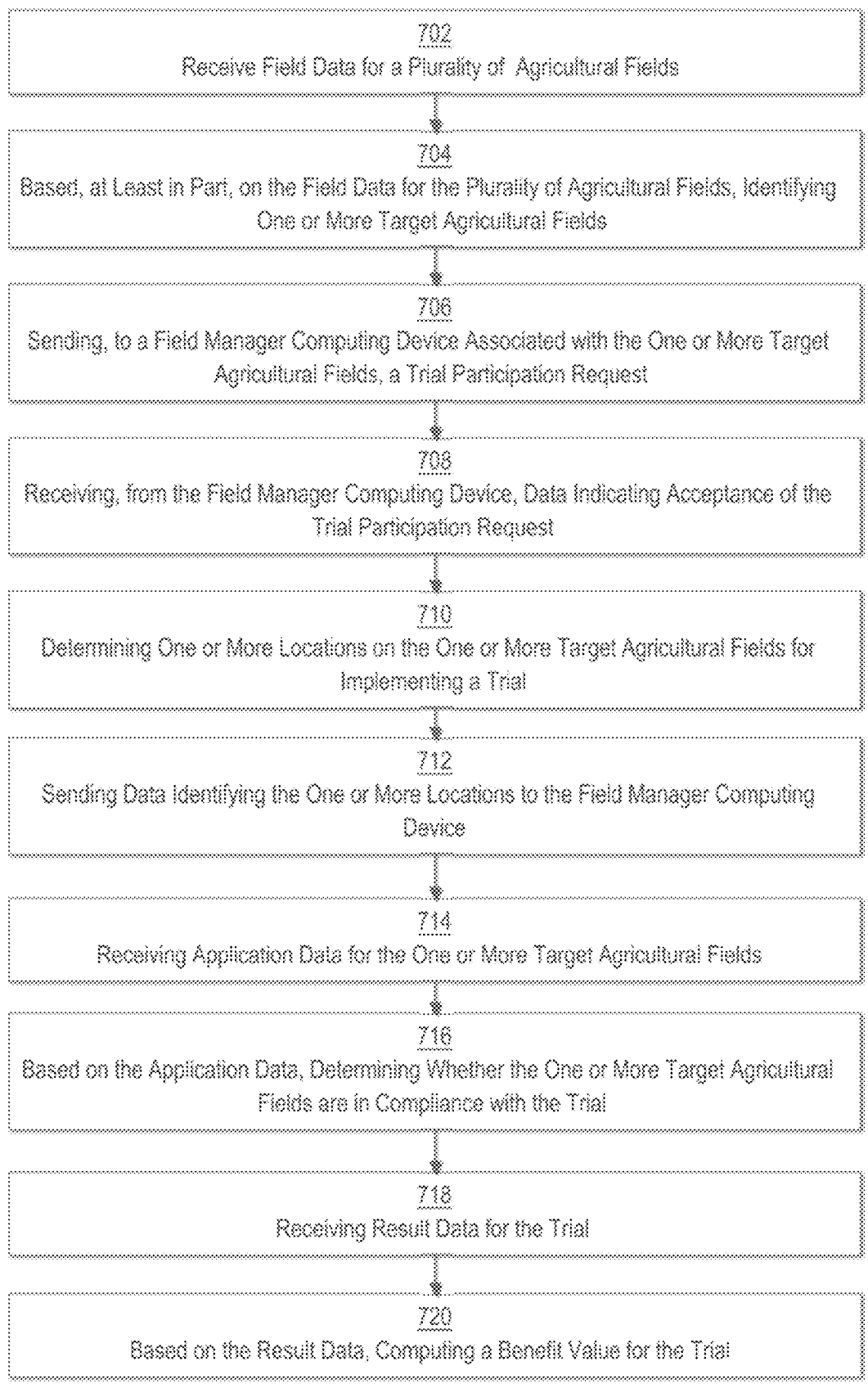
FIG. 7 depicts an example method of implementing a trial. At step 702, field data for a plurality of agricultural fields is received.

FIG. 7 depicts an example method of implementing a trial. At step 702, field data for a plurality of agricultural fields is received at the agricultural intelligence computing system. For example, the agricultural intelligence computing system may track developments on fields associated with a plurality of different field managers. The server may receive data for the plurality of fields over a network from field manager computing devices, remote sensors, and/or external computing systems. Types of field data and methods of obtaining the field data are described further herein.

At step 704, one or more target agricultural fields are identified based, at least in part, on the field data for the plurality of agricultural fields. The agricultural intelligence computing system may be programmed or configured to directly identify fields and/or to identify field manager accounts as target accounts for sending a trial request message. Generally, the agricultural intelligence computing system may select target agricultural fields based on likelihood of acceptance of the trial, likely benefits to the field of performing the trial, likelihood of detecting the benefits to the field of performing the trial, and general applicability of the trial. Methods of identifying fields are described further herein.

At step 706, a trial participation request is sent by the agricultural intelligence computing system to a field manager computing device associated with the one or more target agricultural fields. The trial participation request may identify a product and/or one or more management practices to be undertaken as part of the trial. The trial participation request may additionally include costs or benefits for participating in the trial. Trial participation requests are further described herein.

At step 708, data indicating acceptance of the trial participation request is received from a field manager computing device. For example, the agricultural intelligence computing system may receive, through a graphical user interface executing on the field manager computing device, a selection of an option indicating acceptance of the trial participation request.

At step 710, one or more locations on the one or more target agricultural fields are determined for implementing the trial. The agricultural intelligence computing system may identify locations on the field for implementing a test location based on areas in the field capable of performing the trial, efficiency of performing the trial in each location, applicability of the trial to other locations, and/or benefit to the field of performing the trial. Methods of determining locations for implementing the test location are described further herein.

At step 712, data identifying the one or more locations is sent to a field manager computing device. For example, the agricultural intelligence computing system may cause display of a map on a display of a client computing device where the map identifies one or more test locations along with data indicating the product and/or management practices to be applied to the test location. Additionally or alternatively, the agricultural intelligence computing system may generate one or more scripts for a field implement on the one or more fields that causes the field implement to apply the product and/or management practices in the one or more locations. The data may be accompanied with instructions for implementing the trial. Methods for identifying the one or more test locations to the field manager computing device are described further herein.

At step 714, application data for the one or more target agricultural fields is received by the agricultural intelligence computing system. For example, a field implement and/or remote sensor may measure a population rate as planted, an application of pesticide, fungicide, and/or fertilizer, irrigation, tillage, or any other application of products, management methods, or value associated with the growing of one or more crops. Additionally or alternatively, a field manager may identify management, planting, and/or application practices to the agricultural intelligence computing system through a graphical user interface executing on the field manager computing device.

At step 716, based on the application data, it is determined whether the one or more target agricultural fields are in compliance with the trial. For example, the agricultural intelligence computing system may determine whether a test location of an appropriate size has been implemented in an appropriate position and with the appropriate planting, product, and/or management rules. If the one or more target agricultural fields are not in compliance with the trial, the agricultural intelligence computing system may determine a manner of updating the trial to allow the field manager a chance to be in compliance with the trial. For example, if the field manager planted an incorrect population rate in a location selected for the trial, the agricultural intelligence computing system may identify a new location for implementing part or all of the trial and send data identifying the new location to the field manager computing device.

At step 718, a computing system receives result data for the trial. For example, if the field is either in compliance with the initial trial or updated trial, the agricultural intelligence computing system may receive yield data and/or profit data for both the one more test locations and the one or more other portions of the field. Additionally or alternatively, one or more separate computing devices may perform the steps of computing yield data and computing benefit values prior to sending the benefit values to the agricultural intelligence computer system. The result data may be sent by the field manager computing device and/or by one or more implements or sensors. For example, a satellite image of the one or more fields may be used to compute total yield and/or infer crop status for both the one or more fields and the location of the test locations.

At step 720, based on the result data, a benefit value for the trial is computed. For example, the agricultural intelligence computer system may compute a benefit value as a function of the result data. The benefit value may include a value identifying an increase in yield, an increase in profit, a savings in input cost or time, and/or an increase in quality of the crop. Based on the benefit value, the agricultural intelligence computing system may determine whether to issue a rebate for the trial, request additional funds, or otherwise exchange value with the field manager associated with the field manager computing device.

FIG. 7 depicts one example method of implementing a trial. Other examples may include less or more steps. For example, a agricultural intelligence computing system may perform the steps of FIG. 7 without steps 706 and 708, thereby providing the benefits of the target identification, the location identification, and the tracking of the trial without the interactions with the field manager computing device. As another alternative, the agricultural intelligence computing system may send multiple possible trial types to a field manager computing device with an option to select one or more of the trial types for implementing on the field.

A field manager computing device, as used herein, may act as a communication device between a field manager and the agricultural intelligence computing system and/or as a controller for a field implement. Thus, the agricultural intelligence computing system may send instructions to the field manager computing device which, when executed by the field manager computing device, cause controlling implements on a field to implement a trial and/or gather field data. The direct communication with the field implement may be used to bypass communication with the field manager. For example, in step 712, the data identifying the locations for implementing the trial may be sent to a field manager computing device which acts as a controller for a field implement, thereby causing the field implement to execute the trial in the identified locations. The field manager computing device may include a single computing device that communicates with the agricultural intelligence computing system or a plurality of computing devices which communicated with the agricultural intelligence computing system at different steps of the process. For example, a first computing device may receive the trial participation request in step 706 while a second computing device receives the location data in step 712.

4. Provided Field Data

In an embodiment, an agricultural intelligence computing system communicates with a plurality of field manager computing devices over a network. Each field manager computing device of the plurality of field manager computing devices may be associated with one or more fields. For example, the agricultural intelligence computing system may store account information for a plurality of different user accounts. A field manager computing device may sign into a particular user account to communicate with the agricultural intelligence computing system. The user account may comprise data identifying one or more fields associated with the user account.

The agricultural intelligence computing system may receive data from the field manager computing devices regarding the one or more fields. Additionally or alternatively, the agricultural intelligence computing system may receive information regarding the one or more fields associated with the field manager computing devices from one or more remote sensors on or about the one or more fields, one or more satellites, one or more manned or unmanned aerial vehicles (MAVs or UAVs), one or more on-the-go sensors, and/or one or more external data servers. The data may include field descriptions, soil data, planting data, fertility data, harvest and yield data, crop protection data, pest and disease data, irrigation data, tiling data, imagery, weather data, and additional management data.

Field descriptions may refer to a field location, a total acreage of the field, a shape and boundaries of the field, elevation and topographic variability of the field, tillage history of the field, crop rotation history of the field, disease history of the field, crop protection of the field, farm equipment use history of the field, and data regarding a field operator. The field location may be identified using GPS coordinates or any other data that identifies a location of the field. Topographic variability may include differences in elevation as well as slope, curvature, and one or more compound topographic indices of areas of the field. Tillage history may include tillage type, depth, and/or timing. Crop rotation history may include identification of past crops planted at each spot on a field and/or data identifying whether crop rotation is regular or irregular. Farm equipment use history may include identification of the tilling, planting, application, and harvesting equipment. The field operator data may identify one or more people, operations, or service providers who perform activities on the field.

Soil data may include spatial and/or temporally varying subfield soil moisture, continuous subfield soil temperature, continuous eddy covariance of water on the field, subfield soil texture including class of soil and/or percentage of sand, silt, and/or clay, subfield soil pH, subfield soil organic matter, subfield soil cation exchange capacity, soil testing data including location of soil collection, date of soil collection, sampling procedure, date of processing, identification of processing facility, and/or identification of one or more people processing and/or collecting the soil, additional soil chemistry data, bulk density of the soil, and/or buffer capacity. Soil data may be received through input from a field manager computing device, one or more servers associated with a testing facility, one or more remote or proximal connected sensors, one or more models of soil moisture, soil temperature, and/or other soil chemical or physical parameters, and/or from one or more databases of soil information such as the SSURGO soil database.

Planting data may include a crop type, seed product information such as hybrid data, variety, seed treatments, relative maturity, growing degree days to maturity, disease resistance ratings, and/or standability, depth and row spacing, seed population as planted, seed population as expected, time and date of planting, spatial indexed seed rate, target yield, planting equipment data such as type, capabilities, and dimensions, use or nonuse of a seed firmer, starting fertilizer data, replant data, existence of trials and/or other experiments, and shape and boundaries of planting.

Fertility data may include application dates of fertilizer, type of mixture applied, application location, amount of application and target rate, manure composition, application methods, fertilizer application equipment data such as type, capabilities, and dimensions, and/or cost of application.

Harvest and yield data may include harvest dates and time, yield amount by location and/or field, shell weight for products such as corn, test weight, number of combines used on the field, yield monitor data such as calibration parameters, speed, and header height, elevator measured values such as load wet mass and moisture, stalk integrity, quantified yield loss due to stalk integrity issues, equipment data such as type, capabilities, and dimensions, residue management data such as baling data, early stand count, lodging data including root lodging and stem failure, greensnap data, white mold data, yellow flash data, and/or shape and boundaries of harvesting.

Crop protection data may include date and time of application of crop protection chemicals, application type, chemical makeup of crop protection chemicals and/or adjuvants, carrier volume, application rate of chemicals, carrier solution rate, application location on the field, method of application, user of in-furrow fertilizer and/or insecticide, equipment data such as type, capabilities, and dimensions, and/or cost of application.

Pest and disease data may include subfield pathogen presence in plant tissue, residue, and soil, damage type and extent from biotic stress caused by insects, and/or damage type and extent from biotic stress caused by pathogens. Extent of damage may be identified as low, medium, or high or as one more numeric ratings. Biotic stress and pathogen presence may be measured and/or modeled.

Irrigation data may include presence of irrigation, irrigation system types, irrigation times, amount of irrigation, use of fertigation, and/or type and amount of fertigation.

Tiling data may include presence of tiling, tiling system types, tiling system maps, tiling system flow conductances, and/or flow rates or fluid levels in tile lines.

Imagery may include leaf level photographs of foliar disease and stress, leaf-level and field-level photographs of stressed plants, satellite imagery of a field across one or more visual bands, and/or any other images of a locations on the field. Imagery of the field may additionally include quantifications of damage assigned to portions of the images. Imagery may be based on visible light and/or light bands outside the visual spectrum.

Weather data may include historical, current, and/or predicted rainfall data such as amount of rainfall and location of rainfall, historical, current, and/or predicted temperatures including hourly temperature, temperature maximums and minimums, day time temperatures, and nighttime temperatures, dewpoint, humidity, wind speed, wind direction, solar radiation and sky cover during daytime hours and during nighttime hours, weather impacts on yield, existence of hail, straight line winds, tornadoes, and/or intense precipitation, and/or depth of freeze during winter.

Additional management data may include any additional data relating to the management and care of the crop such as applications, treatments, and observations. Observations may include observed droughts, observed ponding, observed drainage, observed crop cover, and/or observed damage to the crops.

5. Target Identification

Based, at least in part, on data regarding a plurality of fields associated with a plurality of field manager computing devices, the agricultural intelligence computing system may select one or more particular fields for performing experimental trials. The agricultural intelligence computing system may consider factors such as a modeled benefit to a field of implementing the experimental trials, a historical risk tolerance associated with a field, a usefulness of using a field to implement the experimental trials, a likelihood of detecting a benefit to a field of implementing the experimental trials, operational capabilities associated with a field, the use of particular equipment or machinery with a field, and/or identified existing or previous experiments on a field. Each of these factors is described further herein. Additional methods for identifying target fields are described in Section 5.1. of the present application and in U.S. patent application Ser. No. 15/989,944, the entire contents of which is incorporated by reference as if fully set forth herein.

In an embodiment, the agricultural intelligence computing system models a benefit to a field of implementing an experimental trial. For example, the agricultural intelligence computing system may identify one or more fields for performing a fungicide application trial. The agricultural intelligence computing system may identify one or more fields which have been damaged by fungus in the past and/or are likely to be damaged by fungus in the future. The agricultural intelligence computing system may additionally determine that a yield of the field and/or total profit for the field would result or be benefited by application of a particular fungicide. The agricultural intelligence computing system may additionally determine that a yield and/or profit benefit for the field by application of a particular fungicide would likely be detectable based on the size of the yield and/or profit benefit, the variability of the yield and/or profit benefit across the field, and/or the size of the field and the size of the trial or test regions. Based on the determinations, the agricultural intelligence computing system may identify the one or more fields as good candidates for the fungicide application trial.

The agricultural intelligence computing system may model the benefit to the field based on the responsiveness of the field and an analysis of a product's performance. For example, through different trials of the product, the agricultural intelligence computing system may determine that the product, on average, increases yield for responsive fields by a first amount and increases yield for non-responsive fields by a second amount. Responsiveness of fields may be determined based on prior practices and changes in yield. For example, a more responsive field would have a higher change in yield when management practices change while a less responsive field would have a lower variation in yield when management practices change. An agricultural intelligence computing system may determine the responsiveness of different areas for a particular field based on prior practices, prior yield data, and other field data from one or many fields. The agricultural intelligence computing system may then determine the effectiveness of applying the product to the responsive portions and the non-responsive portions of the field.

The agricultural intelligence computing system may identify one or more fields that are at risk of one or more events that may affect crop yield. For example, risk of disease may be based on modeled or measured soil moisture, existence of ponding on the field, measured or modeled ambient temperatures, measured or modeled ambient humidity, recorded or modeled crop genetics, recorded or modeled planting date, satellite imagery of the field, and/or thermal imagery of the field. Examples of identifying fields that are at risk of one or more events are described in patent application Ser. No. 15/820,317 and 15/820,322, the entire contents of both of which are incorporated by reference as if fully disclosed herein.

Additionally, the agricultural intelligence computing system may identify management practices that increase or decrease the risk of the one or more events. Examples for disease control include use of irrigation, crop rotation, tillage methods, plant genetics, and planting rate. Additionally, the agricultural intelligence computing system may identify environmental factors that increase or decrease the risk of the one or more events. Examples for disease control include soil organic matter percentage, soil pH, and other soil nutrient concentrations. The agricultural intelligence computing system may use the environmental factors to determine which fields are at risk and select fields based on the risk percentage or a computed severity of risked damage.

While embodiments are described with respect to application of specific products, fields may additionally be identified based on other possible benefits to the field from one or more recommendations. For example, if the agricultural intelligence computing system determines that a higher seeding rate in a particular area of a field is likely to increase the yield of the crop, the agricultural intelligence computing system may select the field for performing a seed rate increase trial.

Fields may additionally be identified based on the uniformity, variability and predictability of their yield data. For example, if the agricultural intelligence computing system determines that a field has low yield variability on short length scale and/or in zones, and higher yield variability on longer length scales and/or between zones, the agricultural intelligence computing system may select the field and/or specific zones for performing a trial.

In an embodiment, the agricultural intelligence computing system determines a historical risk tolerance associated with a field. For example, prior practices for a field may indicate that a field manager has a higher tolerance for risk-laden activities that may increase the average yield for the land. Examples of practices that indicate a higher risk tolerance include planting fewer hybrids or varieties of seeds, planting hybrids or varieties designed to produce higher yields under optimal conditions but produce lower yields under non-optimal conditions, a historical tendency to underapply pest-control measures compared to best management practice, a percentage of the field where a new product is planted for the first time, a number of experiments on the field, higher seeding population used than averages for a surrounding county or area, widely different seed selection or seed trait package than typical for a surrounding county or area, relatively advanced and/or potentially unproven types of equipment, for example variable rate capabilities, application equipment capable of late season nitrogen, and/or active downforce management systems on planter, and references to riskier activities on social media. Additionally, the agricultural intelligence computing system may receive survey data from field manager computing devices indicating a risk tolerance with respect to one or more fields.

Risk tolerance may also be indicated by a field manager opting into one or more prior trials. For example, if a field manager has agreed to perform a trial during a prior season, the agricultural intelligence computing system may identify the field as a good candidate for a current trial. Additionally or alternatively, the agricultural intelligence computing system may store a list of accounts, fields, and/or field managers who have indicated an interest in participating in future trials. For example, the agricultural intelligence computing system may cause display of an interface on a field manager computing device that requests an indication as to whether a field manager would be willing to participate in future trials. If the agricultural intelligence computing system receives a positive indication, the agricultural intelligence computing system may update the list to indicate that the field manager has indicated a willingness to participate in future trials.

The agricultural intelligence computing system may be programmed or configured to consider these factors individually and/or in combination. For example, the agricultural intelligence computing system may be programmed to identify fields with a highest percentage of the field dedicated to a new product. Additionally or alternatively, the agricultural intelligence computing system may be programmed or configured to select fields that include more than a threshold number of experiments and are associated with one or more other risky activities. In an embodiment, the agricultural intelligence computing system computes a risk tolerance value. The risk tolerance value may be computed as a function of any of the above factors. As a simple example, a risk tolerance equation may comprise:

$$R_t = S + N + E_x + D + Y + E_q + M$$

where $R_t$ is the risk tolerance, S is a value which increases based on the existence of particular traits in the seeds, N is a value which increases with based on the percentage of the field with a new product, $E_x$ is a value which increases with a number of identified experiments on the field, D is a value which increases as the difference in seeding population between the field and the average for the county increases, Y is a value which increases based on the predictability of the yield variability, $E_x$ is a value which increases based on the existence of particular types of equipment, and M is a value which increases with references to risky activities on social media. These factors may be weighted such that certain factors are considered more heavily than others. While the example shown above is additive, other embodiments may include other methods of estimating risk, such as a multiplicative risk tolerance equation, such as:

$$R_t = S * N * E_x * D * Y * E_q * M * R_0$$

where $R_0$ is a base risk rate.

In an embodiment, the agricultural intelligence computing system determines a usefulness of using a field to implement the experimental trials. The usefulness of using the field refers to an applicability of the trial to one or more other locations. For example, trials may be less useful when performed on a field with unique characteristics such that the benefits of the tested action are not applicable to a wider array of locations. Thus, the agricultural intelligence computing system may be programmed to identify fields with characteristics similar to other fields for the purpose of particular trials. For example, for a fungicide trial, the agricultural intelligence computing system may identify fields with similar ponding conditions, average temperatures, soil moisture, and rainfall as other fields. As another example, a field for a fertilizer trial may be selected based on soil conditions, such as percent of sand, silt, and clay, being similar to soil conditions of other fields in the area.

The agricultural intelligence computing system may additionally determine usefulness based on data indicating planned practices. The data indicating planned practices may be received directly from a field manager computing device and/or inferred from prior practices. For example, the agricultural intelligence computing system may store prior planting data for a field indicating that a particular hybrid of a crop has been planted on a particular field for the last three years. Based on the stored prior planting data, the agricultural intelligence computing system may determine that the particular hybrid has been planted on the particular field for the last three years. The agricultural intelligence computing system may then determine that a different hybrid may increase crop yield, cost less, increase crop quality, and/or otherwise benefit the particular field over the particular hybrid.

Applicability of the trial to one or more other locations may be based on past events for the field. For example, the agricultural intelligence computing system may identify a plurality of fields that had a low yield due to a particular pest. The agricultural intelligence computing system may identify one or more fields of the plurality of fields as candidates for the trial based on the one or more fields having suffered an approximately average loss of yield due to the particular pest.

In an embodiment, the agricultural intelligence computing system determines the operational capabilities associated with a field. For example, a field manager computing device may send data to the agricultural intelligence computing system regarding devices on the field. The data may indicate types of devices, capabilities of devices, and number of devices. If the agricultural intelligence computing system determines that the devices on a field do not match device requirements for a trial, the agricultural intelligence computing system may not select the field. For example, a field manager computing device may determine two combines are used on a field of a particular size. If a trial requires a maximum of one combine harvester for a field of the particular size, the agricultural intelligence computing system may not select the field as a candidate for participation in the trial.

In an embodiment, the agricultural intelligence computing system identifies evidence of existing or previous experiments on a field. Based on the evidence of existing or previous experiments on the field, the agricultural intelligence computing system may select the field as a candidate for performing a trial. The agricultural intelligence computing system may identify evidence of experiments based on sections of a field that are treated differently from the rest of the field. For instance, the agricultural intelligence computing system may identify locations in the field that have received different seed types, seeding populations, and/or product applications such as fertilizer and pesticide. If a determination is made that a field contains one or more experiments, the agricultural intelligence computing system may select the field as a candidate for participation in the trial.

The above factors may be binary determinations and/or quantitative computations. Binary determinations for the above described factors may be defined by satisfaction of one or more conditions. For example, the agricultural intelligence computing system may determine whether or not there are current experiments on the field, whether or not the devices on the field are capable of performing a trial, whether or not the features of a field are within a particular range, whether a modeled benefit to the field is greater than a threshold value, whether a modeled likelihood of detecting a benefit to the field is greater than a threshold value, and/or whether or not a risk value for a field exceeds a particular threshold value. In response to satisfaction of one or more conditions, the agricultural intelligence computing system may identify the field for performance of a trial. For instance, if the only requirement is a risk value over a threshold value, then the agricultural intelligence computing system may select the agricultural field if the risk value is above the threshold value. If the agricultural intelligence computing system utilizes two requirements, the agricultural intelligence computing system may select the agricultural field if both requirements are met.

As another example, the agricultural intelligence computing system may compute a value as a function of a risk tolerance value, a value describing the similarity of the field to other fields, and a value describing the benefit of participating in the trial. The benefit value may be computed as a modeled gain in yield and/or profit from participating in the trial. The similarity value may be computed as a function of differences in one or more attributes of the soil, weather, or other field values between the field and average values for other fields. The agricultural intelligence computing system may determine if the computed value is above a stored threshold value and, in response to determining that the computed value is above the stored threshold value, select the agricultural field for performing the trial.

While the above examples describe selection of agricultural fields based on absolutes, such as one or more values exceeding a threshold value, in some embodiments the agricultural fields are selected based on a comparison of values to other agricultural fields. For example, the agricultural intelligence computing system may select one or more agricultural fields that have the highest benefit values compared to the remainder of agricultural fields for which benefit values were computed. The comparative values may be combined with binary determinations. For example, the agricultural intelligence computing system may identify a group of all agricultural fields with a risk value above a particular threshold value and select from the group one or more agricultural fields with the highest benefit values compared to the remainder of the agricultural fields of the group. As another example, the agricultural intelligence computing system may identify a group of all agricultural fields with a predicted benefit value above a particular threshold value and select from the group one or more agricultural fields with the highest likelihood of detecting a benefit compared to the remainder of the agricultural fields of the group.

In some embodiments, a field may be selected for performing a trial based, at least in part, on a request from a field manager computing device. For example, the agricultural intelligence computing system may provide a graphical user interface to a field manager computing device with options for requesting placement into a trial. In response to receiving input from the field manager computing device selecting the option, the agricultural intelligence computing system may utilize the methods described herein to identify one or more trials for an agronomic field corresponding to an account of the field manager computing device.

Figure 13:
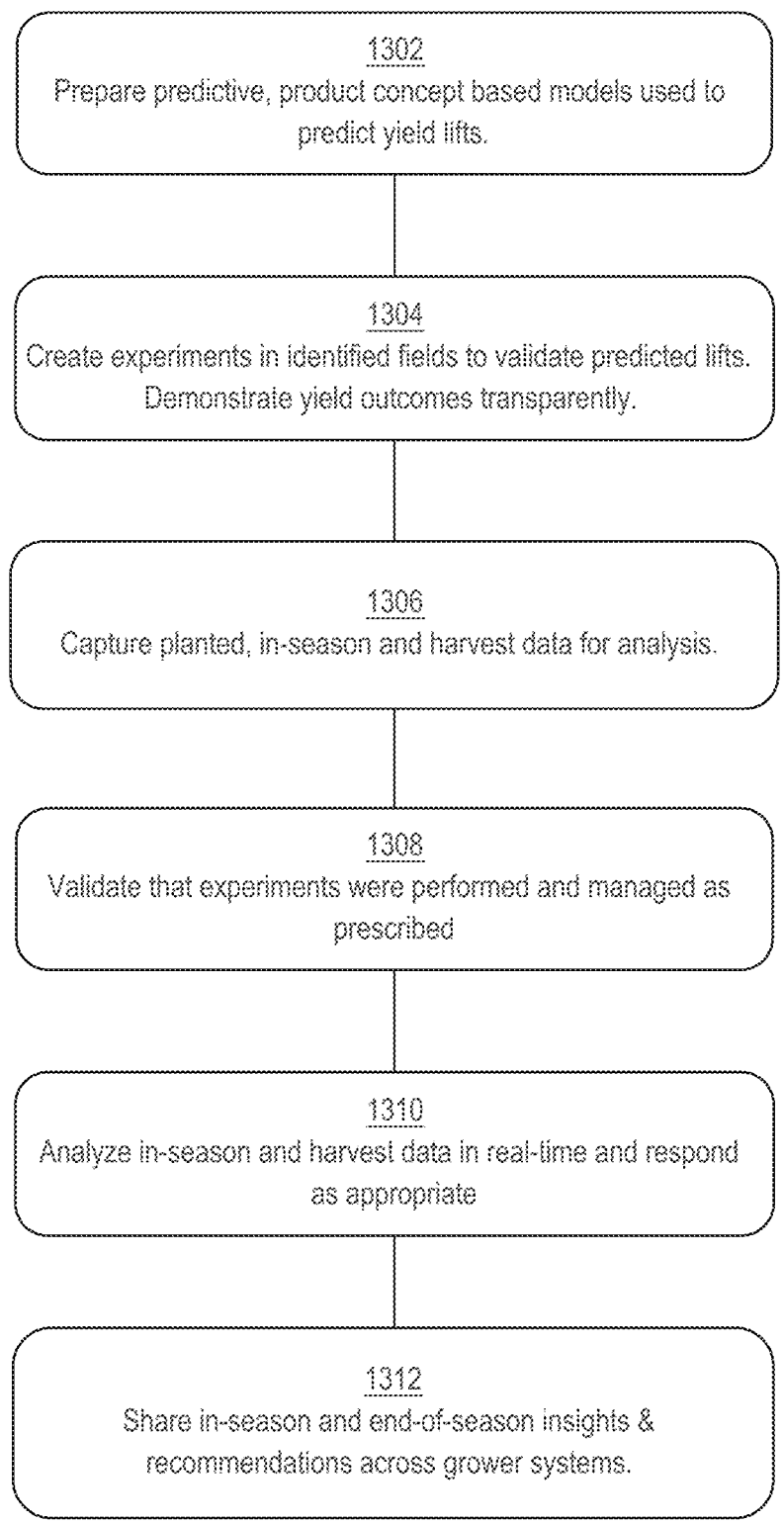
FIG. 13 illustrates an example process performed by the field study server from field targeting to information distribution across grower systems.

5.1. Example Target Identification Implementation 5.1.1. Cross-Grower Field Study FIG. 13 illustrates a process performed by the agricultural intelligence computer system from field targeting to information distribution across grower systems. In some embodiments, the system 130 is programmed to perform automated cross-grower analysis, which can comprise computationally targeting grower fields, prescribing experiments to grower fields, collecting data from prescribed experiments, validating execution of the prescribed experiments, analyzing the collected data, and distributing analytical results across grower systems.

In step 1302, the system 130 prepares predictive, produce concept based models used to predict yield lifts. In some embodiments, given relevant data regarding a list of grower fields, the system 130 is programmed to design specific experiments for specific grower fields. The objective of an experiment is typically to increase the yield of one or more fields by a certain level, although it can also be related to reducing the inputs or an improvement of any other aspect of the fields. The design of an experiment or specifically a targeted trial (to be distinguished from a controlled trial, as further discussed below) includes determining which attributes of a field might be related to an experimental objective and how a change in the values of some of those attributes might help achieve the experimental objective. One example experiment is to increase the seeding rate of a field by an amount in order to increase or lift a crop yield by a certain amount. Another example experiment is to increase the fungicide usage of a field by an amount in order to achieve a reduction in disease spread by a certain amount.

In some embodiments, the system 130 is programmed to manage the list of grower fields at a granular level. The system 130 is therefore configured to identify certain boundaries or other problematic areas of the fields that will not participate in prescribed experiments, and further determine specific strips or squares, with buffer areas in between, that will participate in prescribed experiments.

As an example, to determine for which portions of which fields to increase the seeding rate by a certain amount or by what amount to increase the seeding rate for specific fields, the system 130 can be configured to evaluate, for each field, the hybrid or variety of crop types, the current seeding rate, the historical yearly yield, how a change in seeding rate affected the yield in the past, how the seeding rate was affected by weather or other variables, or other factors affecting the field. While it is called an experiment, the system 130 is configured to predict the outcome of the experiment and determine whether to apply the experiment based on the predicted outcome. For example, the system 130 can be configured to apply only those experiments with highest predicted yield lifts in the study. Therefore, each experiment essentially includes a recommendation, such as increasing the seeding rate by a certain amount, that is to be validated.

In some embodiments, targeting grower fields also involves the design of multiple experiments to be applied to the fields of one or more growers in a coordinated fashion. For example, a single field can be divided into multiple locations for planting multiple hybrids or varieties of a crop. While different fields might specifically benefit from different experiments at a certain time, the collection of all the fields can benefit from coordinated experiments so that as much analytical insight can be shared across grower fields as possible for long-term benefits. For example, some growers might have a limited number of fields where only a limited number of experiments involving a small number of attributes or a small number of values for a certain attribute can apply this year. Those fields can then benefit from the application of additional experiments to other growers' fields that involve different attributes or different values for the same attributes.

In some embodiments, the system 130 is programmed to start designing, selecting, or applying experiments in response to specific triggers. Such triggers may include when a field is under-performing (e.g., low crop biomass or low predicted crop yield within a certain timeframe), when a field is in an unusual condition (e.g., low soil moisture or nitrate), when a change occurs in the environment (e.g., extreme heat wave), or when an experiment prescribed to a similar field has produced a certain outcome. These triggers can be detected from the data collected during the implementation of the prescribed experiments, as further discussed below. Each trigger generally represents an opportunity to improve the performance of a field or gain specific insight into certain agricultural phenomena or relationships.

In step 1304, the system 130 is programmed to prescribe experiments to grower fields. In some embodiments, the design or selection of experiments can be carried out automatically according to a predetermined schedule, such as at the beginning of every year or every growing season. The prescribing of experiments can also be performed automatically. The system 130 can be configured to generate the prescription, plan, or scheme for an experiment that is to be understood by a human, a machine, or a combination of both. For example, one experiment may be to plant certain seeds at certain rates on a certain grower's fields. The plan for the experiment can include a variety of details, such as the type of seeds, the destination of the seeds within the fields, the volume of seeds to plant each day, or the time to plant the seeds each day.

In some embodiments, the prescription or scheme also includes details for implementing a control trial as opposed to the targeted trial (the original, intended experiment), to enable a grower to better understand the effect of the targeted trial. Generally, the control trial involves a contrasting value for the relevant attribute, which could be based on what was implemented in the field in the present or in the past. For example, when the targeted trial is to increase the seeding rate by a first amount to increase the yield by a certain level, the control trial may be to not increase the seeding rate (maintaining the present seeding rate) or to increase by a second amount that is higher or lower than the first amount. The prescription can include additional information, such as when and where the targeted trial and the control trial are to be implemented on the grower's fields. For example, in one scheme, a grower's field can be divided into locations, and the prescription can indicate that the first location is to be used for the targeted trial, the second location is to be used for the control trial, and this pattern is to repeat three times geographically (the second time on the $3^{rd}$ and fourth locations, and the 3 time on the $5^{th}$ and the sixth locations). The prescription can generally incorporate at least some level of randomization in managing the targeted trial and the control trial, such as randomly assigning certain locations to either trial, to minimize any bias that might exist between the two trials.

In some embodiments, the system 130 is programmed to transmit the plan directly to the agricultural implements of the relevant fields, such as a seed dispenser or another planter registered under the grower of the fields or associated with the specific fields. Depending on how smart the planter is, the planter may automatically implement at least some of the experiment according to the plan or at least display the plan to the grower as the grower manually operates the planter. For example, the plan can be translated into electronic signals for controlling the wakeup time of the planter, the moving or rotational speed of the planter, or the route taken by the planter. Alternatively, the system 130 can be programmed to transmit the plans or schemes for the experiment to other smart devices registered under the grower, such as a mobile device, to the extent that part of the plan needs to be implemented manually or simply for informational purposes.

In some embodiments, instead of transmitting the entire scheme for an experiment to a smart device, whether it is an agricultural implement or a person digital assistant, the system 130 is programmed to transmit the scheme incrementally and timely. For example, when the scheme involves the performance of daily tasks, the system 130 can be configured to send a portion of the scheme corresponding to each day's work every day. The system 130 can also be configured to deliver reminders to the grower's mobile devices, for example, for the performance of certain tasks according to the scheme.

In step 1306, the system 130 is programmed to collect data from prescribed experiments. In some embodiments, the system 130 is programmed to receive data from the same agricultural implements to which the experiment schemes or plans were transmitted, or from the same field manager computing device, including mobile devices, registered under the growers. The agricultural implements can be equipped with sensors that can capture many types of data. In addition to data related to the variables involved in the experiment, such as the volume of seeds actually planted, the time of actual planting, the actual moving or rotational speed of the agricultural implement, the route actually taken by the agricultural implement, or the crop yield actually achieved, an agricultural implement can capture additional data related to the weather, such as the amount of sunlight, humidity, pollen, wind, etc. The agricultural implement can also record additional data related to its internal state, including whether different components are functioning properly, when the agricultural implement is cleaned or maintained, how often the agricultural implement is used, or whether the agricultural implement is used in any unusual manner. Some of these types data can be observed by sensors integrated with personal computing devices or directly by growers and subsequently reported via the personal computing devices to the system 130. In general, the data can be transmitted by an agricultural implement or a personal computing device to the system 130 once the data becomes available, upon request by the system 130, or according to a predetermined schedule.

In step 1308, the system 130 is programmed to validate execution of the prescribed experiments. In some embodiments, the system 130 is programmed to determine whether the prescribed experiment is properly carried out according to the plan or scheme for the experiment. The objective is to enable proper implementation of the prescribed experiments in order to achieve the predicted results. For the variables involved in the scheme, the system 130 is programmed to compare the actual value, such as the volume of seeds actually planted at a specific location within a particular period of time, such as one hour, and the prescribed value. The system 130 is configured to report any detected discrepancy. For example, at least a warning can be sent to the grower's personal computing device that if the plan is not strictly followed, the expected benefit of the prescribed experiment will not be achieved. A warning may appear in any form known in the art such as a pop-up, instant message, e-mail or other text message. The warning could alternatively be presented as a static or moving or flashing visual or graphic such as a color coded visual such as a green light indicating that the experiment is in compliance or red light showing non-compliance. Compliance (or non-compliance) could also be based on a whether a value falls within a pre-determined tolerance or range. For example, the agricultural intelligence computer system may determine whether a compliance level is below a threshold value. For instance, if the compliance level relates to a percentage of a location that is in compliance, the system may determine whether the percentage of the location in compliance is below 90%.

In some embodiments, the system 130 is programmed to evaluate other collected data and recommend remedial steps. Specifically, the system 130 can be configured to transmit a series of steps for diagnosing whether a component of the agricultural implement is functioning properly. For example, when the volume of seeds actually planted at a specific location within a one-hour span is greater than the prescribed value, the bin holding the seeds to be planted or the scale for weighing the seeds to be planted may be out of order. Therefore, the system 130 might be programmed to request an inspection of the bin or the scale. When the malfunctioning of the agricultural implement is detected directly by sensors or through certain diagnosis, the system 130 can be programmed to transmit a similar recommendation for recalibrating or repairing the agricultural implement. On the other hand, upon a determination that certain steps are completely skipped, the system 130 can be programmed to transmit an instruction to follow those steps, or a suggestion for readjusting reminder alarms or for inspecting the agricultural implements.

In some embodiments, the system 130 can be programmed to validate the execution of each prescribed experiment according to a predetermined schedule, such as every month, or as soon as error signals or application data are received. The system 130 can also be programmed to validate the execution of all prescribed experiments according to a specific paradigm, such as one based on randomly sampling, in order to conserve resources.

In step 1310, the system 130 is programmed to analyze the collected data. In some embodiments, the system 130 is programmed to further analyze the data, to adjust the predictions or the plans for the prescribed experiments, or to glean specific insight that can be used in designing future experiments. Such analysis can be performed periodically, at the end of a season or a year, or upon request by a grower.

In some embodiments, when a prescribed experiment was not properly carried out, the predicted result might not be obtained, and the system 130 can be programmed to adjust the prediction based on how the plan for the prescribed experiment was followed. For example, the system 130 can be configured to consider that the actual seeding rate was only 80% of the prescribed seeding rate overall, due to erroneous calibration of the agricultural implement, the skipping of certain planting steps, or other reasons, in determining the predicted crop yield might be only 80% of or otherwise less than the predicted or recommended crop yield. The system 130 can also be programmed to generate a series of remedial steps in order to realize the original prediction. For example, when the actual seeding rate was only 80% of the prescribed seeding rate overall, the system 130 can be configured to compensate for it by prescribing a seeding rate that was 20% or otherwise higher than originally prescribed for the rest of the experiment.

In some embodiments, the system 130 can be programmed to determine why even when the prescribed experiment was properly carried out, the predicted outcome was not achieved. The comparison of the data respectively gathered from the targeted trial and the control trial can often be used to eliminate certain factors from consideration. The system 130 can also be configured to detect correlations between the objective of the experiment and other field attributes or external variables. The system 130 can also be configured to detect patterns from the outcomes of similar experiments, which can help identify outliers and point to field-specific issues. The reasons behind the discrepancies between the predicted outcomes and the actual outcomes can be used for designing future experiments or generating predictions for future experiments. For example, upon detecting a significant correlation between the crop type and the seeding rate with respect to the crop yield, the system 130 can be configured to target specific fields in which certain types of crops are typically grown for an experiment that relates a seeding rate to the crop yield. Similarly, the system 130 can be programmed to predict different levels of crop yield depending on the types of crops grown in the specific field.

In some embodiments, the system 130 is programmed to design incremental experiments. To test a relatively new hypothesis, the system 130 can be configured to prescribe conservative experiments by introducing a relatively small change to one of the attributes or variables. When the actual outcome of the last prescribed experiment agrees with the predicted outcome, the system 130 can be programmed to then introducing further change to the attribute to variable. In other embodiments, the system 130 is programmed to consider the outcomes of two prescribed experiments that were applied to two similar fields and determine whether combining the two experiments might be permissible and beneficial. For example, when the relationship between the seeding rate and the yield and between the soil moisture and the yield have been clearly and separately demonstrated in two similar fields, a future experiment might be to increase the seeding rate and the soil moisture in the same experiment applied to the same field.

In step 1312, the system 130 is optionally programmed to distribute analytic insights across grower systems. In some embodiments, the system 130 is programmed to present summaries, tips, or further recommendations generated from analyzing the data obtained from the multitude of prescribed experiments across grower fields. The system 130 can be configured to transmit a report to each grower system, such as the grower's mobile device, that shows aggregate statistics over all the prescribed experiments or certain groups of prescribed experiments. The report can also indicate how the grower's fields have performed compared to the other growers' fields and indicate possible reasons based on an analysis of the difference in performance between the grower's fields and the other growers' fields. The report can highlight other prescribed experiments that are similar to the ones prescribed to the grower's fields. The report can also outline possible experiments to apply to the grower's fields in the future and solicit feedback from the grower.

In some embodiments, some or all of these steps 1302 through 1312 can be executed repeatedly, iteratively, or out of order. For example, data capturing and execution validation can take place periodically during a season.

5.1.2 Field Targeting

Figure 14:
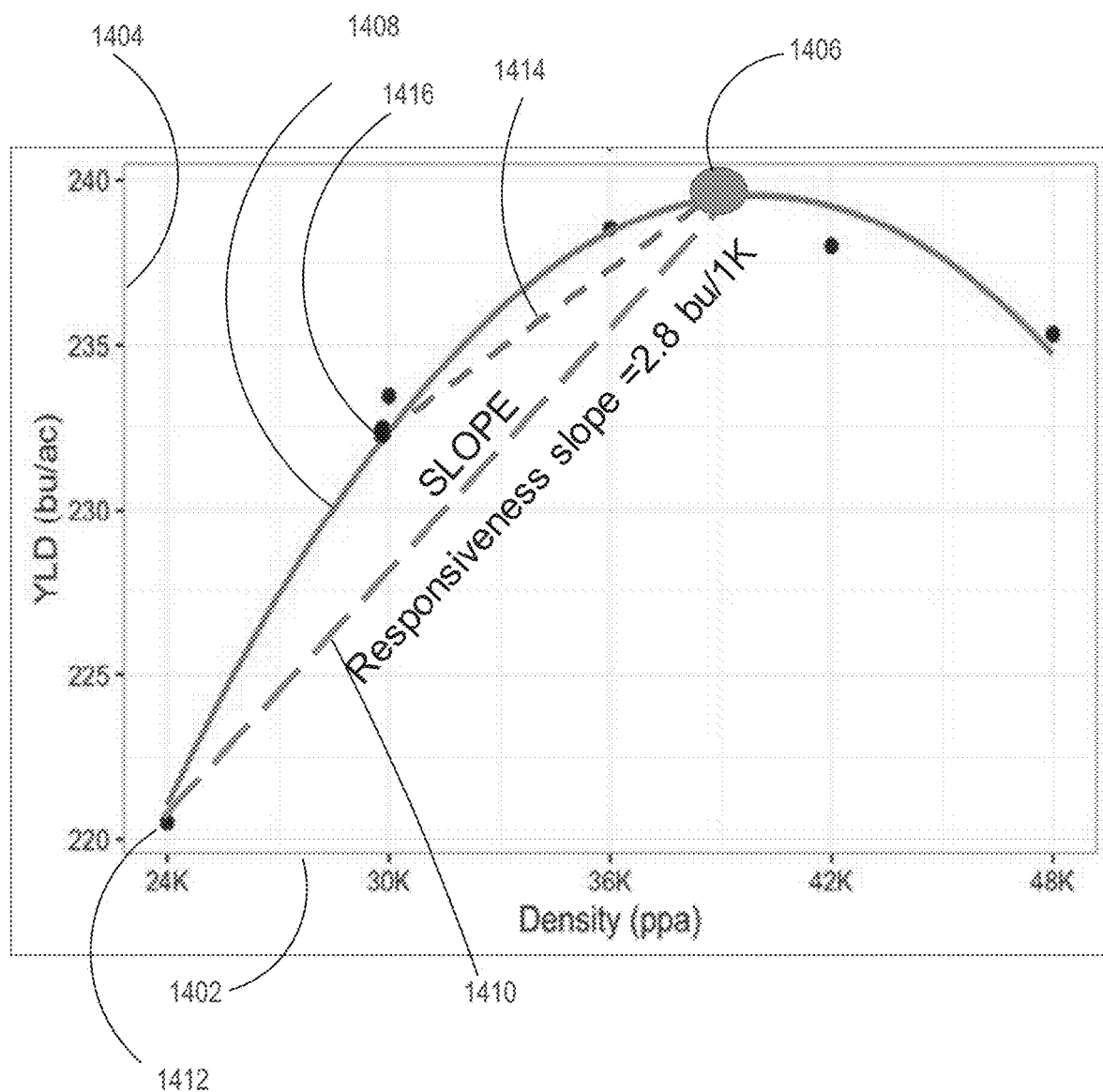
FIG. 14 illustrates an example relationship between the crop density and the crop yield for a given hybrid.

In some embodiments, the system 130 is programmed to build a model comprising computer-executable instructions for predicting product (crop yield) responsiveness of a field to a change in seeding rate. The system 130 is programmed to initially establish certain baselines from historical data that spans a number of years of a number of fields across different growers associated with different grower devices. The historical data can be obtained from internal trials and experiments or from external data sources. The number of fields can have common values in certain characteristics, such as the crop hybrid grown in a field, the location of a field, or the yield lift management practice for a field, as further discussed below. An average relationship between the crop density and the crop yield for a given hybrid can be computed from the historical data to provide a benchmark. Such a relationship is typically reflected in a quadratic curve. FIG. 14 illustrates an example relationship between the crop density and the crop yield for a given hybrid. The X-axis 1402 corresponds to the crop density or seeding rate in plants per acre (ppa), and the Y-axis 1404 corresponds to the crop yield in bushels per acre. In this example, the seeding rate data and the corresponding crop yield data is fitted into a quadratic curve 1408. The shape and size of the quadratic curve 1408 can be characterized by the slope line 1410 from the data point 1412 corresponding to the lowest seeding rate to the data point 1406 corresponding to the optimal seeding rate and the highest crop yield. The system 130 can be programmed to select a threshold for product responsiveness based on the average relationship between the crop density and the crop yield. For example, as the slope of the slope line 1410 here is about 2.8, the threshold can be set to 1.5, so that a field producing a 1.5 bushel yield lift for every 1,000 seed increase would be considered responsive, as further discussed below.

In some embodiments, instead of focusing on reaching the optimal seeding rate, the system 130 is programmed to allow flexibility in seeding rate increase. Specifically, instead of focusing on the relationship between the current seeding rate and the optimal seeding rate, the system 130 is configured to consider other factors, such as a target seeding rate less than the optimal seeding rate or a crop yield lift corresponding to a change to the target seeding rate. For example, the system 130 can be configured to cluster certain fields by hybrid and by location, and compute the average seeding rate within a cluster as the target seeding rate. The same threshold determined from the slope line noted above could still apply in evaluating product responsiveness with respect to the target seeding rate.

In some embodiments, the system 130 is configured to adopt a more complex approach, such as building a decision tree that classifies given fields with seeding rate data and crop yield data into different classes corresponding to different crop yield lift amounts based on the initial (current) seeding rate, the target seeding rate, the difference between the initial seeding rate and the target seeding rate, or other attributes related to the fields. Examples of the other attributes could range from inherent attributes, such as soil moisture level, to environmental attributes, such as soil management practice. Other machine-learning methods known to someone skilled in the art for capturing various relationship between the seeding rate (in conjunction with other attributes) and the crop yield lift, such as neural networks or regression techniques, can also be used. The more complex approach can produce more granular information beyond whether a lift is possible and towards how much lift might be possible.

In some embodiments, the system 130 is programmed to next determine grower-specific product responsiveness. For a grower's field, the system 130 is programmed to similarly review the historical crop yield data over a number of years for a specific zone within the field or the field on average and identify the hybrid and current seeding rate for the field or zone. Referring back to FIG. 14 illustrating the relationship between the crop density and the crop yield for an appropriate hybrid, the slope threshold discussed above, such as 1.5 based on the slope for the first slope line 1410, can be used to determine whether the grower's field is likely to be responsive to a certain seeding rate increase. For example, a second slope line 1414 can be formed from the data point 1416 corresponding to the current seeding rate and the data point 1406 corresponding to the optimal seeding rate and the highest crop yield. When the current seeding rate is smaller than the optimal seeding rate, the slope of the second slope line will be positive but could be above or below the threshold noted above. The system 130 can be configured to deem the field responsive to a seeding rate increase to the optimal seeding rate when the slope of the second slope line is at or above the threshold. When the current seeding rate is larger than the optimal seeding rate, the slope of the second slope line will be negative. The system 130 can then be configured to evaluate the product responsiveness of the field to a seeding rate decrease. The system 130 can be configured to similarly evaluate the product responsiveness of the field to a seeding rate increase to a target seeding rate less than the optimal seeding rate.

In some embodiments, the system 130 is programmed to apply one of the more complex approaches, such as the decision tree discussed above, to evaluate grower-specific product responsiveness. At least the current seeding rate of a grower's field and an intended or target seeding rate for the grower's field could be fed into the decision tree, and a range of crop yield lift values can be estimated by the decision tree, which can be further categorized into responsive or unresponsive or other granular or different classes.

Figure 15:
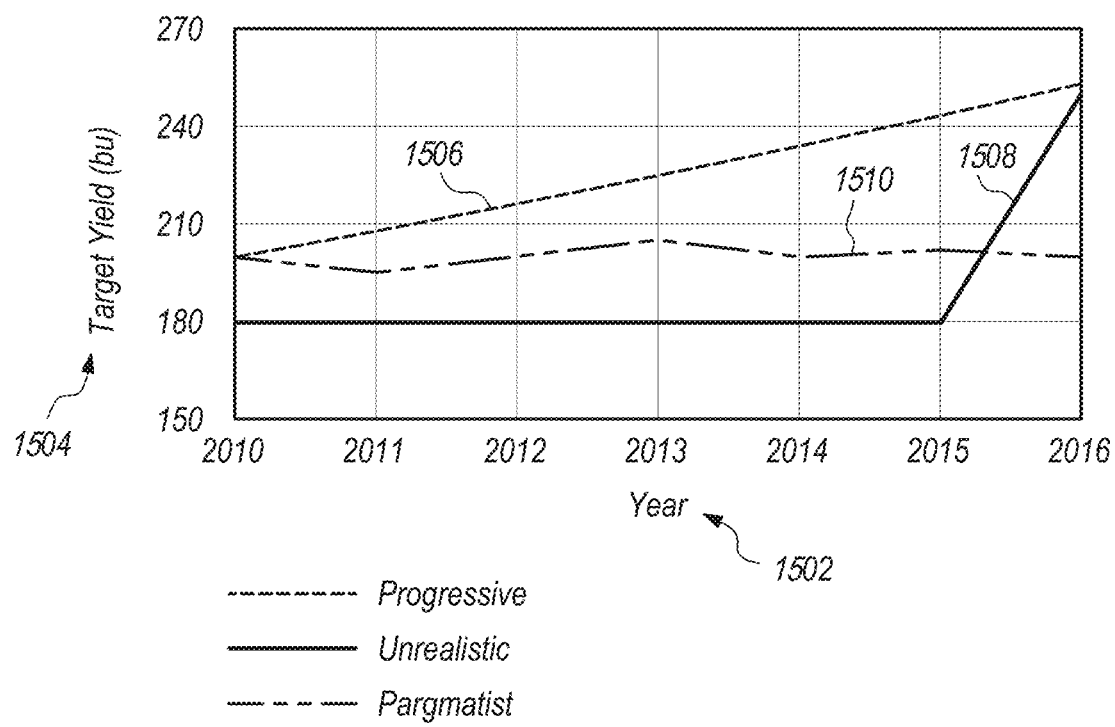
FIG. 15 illustrates example types of management practice.

In some embodiments, the system 130 is programmed to evaluate the grower's field management practice in terms of lifting crop yield over time. FIG. 15 illustrates example types of management practice. The X-axis 1502 corresponds to the year, the Y-axis 1504 corresponds to the target or actual crop yield. The type of management practice in terms lifting crop yield can be reflected in various curves. The curve 1506 indicates an aggressive type, where there is steady and significant increase in crop yield one year after another. The curve 1508 indicates a conservative or pragmatic type, where there is no significant increase in crop yield from one year to the next. The curve 1510 indicates an unrealistic type, where there is no change in crop yield for some years but then there is a sharp increase. Identifying the type of management practice or other aspects external to the soil can be helpful in prescribing actual experiments to targeted growers' fields. In other embodiments, the type of management practice can also be an input attribute for a machine learning method discussed above.

In some embodiments, the system 130 is programmed to also evaluate the degree of variability within the grower's field. Actual density data might be available for different zones within the field, or aerial images of the field can be analyzed via image analysis techniques known to someone skilled in the art. Based on such data, the system 130 can be programmed to determine whether the crop densities or seeding rates are more or less constant across the field or vary substantially among different zones. Such determination can also be useful in prescribing actual experiments to targeted growers' fields.

Figure 16:
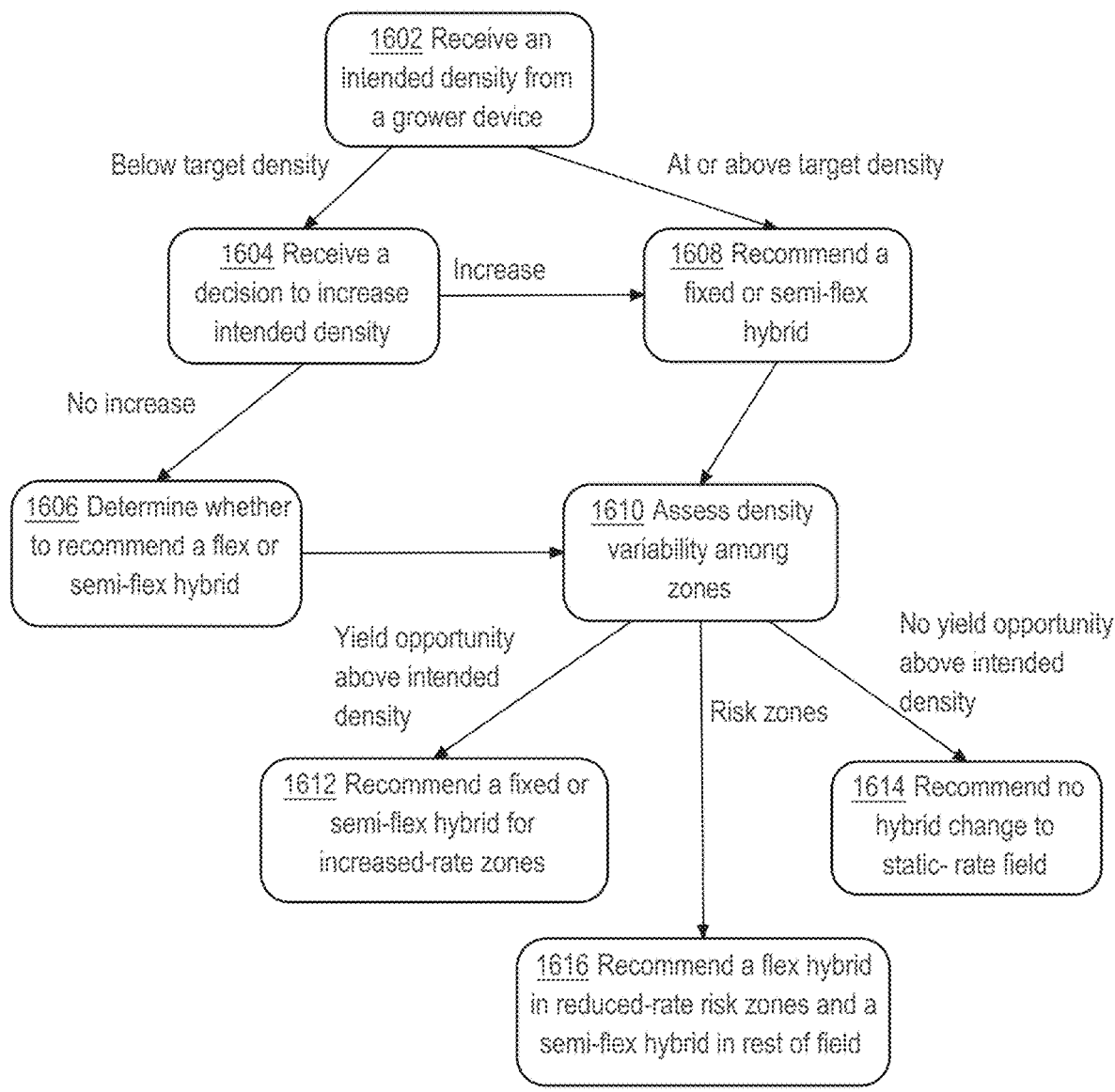
FIG. 16 illustrates an example process performed by the field study server to determine the crop hybrid for a grower's field or the zones thereof.

In some embodiments, the system 130 is programmed to target those growers' fields that are responsive to increasing seeding rates and design experiments for those fields. Each design can have various parameters, such as the crop hybrid, the zone variability, or the seeding rate increase. FIG. 16 illustrates an example process performed by the agricultural intelligence computer system to determine the crop hybrid for a grower's field or the zones thereof. In some embodiments, in step 1602, the system 130 is programmed to communicate with a grower device associated with a targeted field. Specifically, the system 130 is configured to receive an intended density or seeding rate for the field from the grower device. The intended density is typically larger than the current aggregate density in the field. The system 130 is programmed to then determine how the intended density compares with a target density for the field. The target density may be predetermined for the field based on a combination of approaches, such as a comparison with a computed average or optimal seeding rate, a classification via an established seeding-rate decision tree, or an evaluation of the type of management practice in terms of lifting crop yield, as discussed above. The target density is also typically larger than the current aggregate density in the field. When the intended density is below the target density, in step 1604, the system 130 is configured to then receive a decision regarding whether to increase the intended density to the target density from the grower device. When the decision is not to increase the intended density, in step 1606, the system 130 is configured to compute the difference of the intended density from the target density. When the difference is above a certain threshold so that the intended density remains sufficiently low, the system 130 is configured to recommend a flex or semi-flex hybrid for the field. For example, the certain threshold can be 80% of the target density. In some embodiments, when the intended density is at or above the target density reaching a substantially large value, in step 1608, the system 130 is configured to recommend a fixed or semi-flex hybrid for the field.

In some embodiments, the system 130 is programmed to next respond to zone variability within the targeted field. Specifically, in step 1610, the system 130 is configured to determine whether there is significant variability in seeding rates among different zones within the field and whether the current aggregate density considered so far is merely an aggregate across the field. The system 130 may be configured to further determine whether a certain zone may benefit from higher seeding rates from the intended seeding rate, based on the difference between the current seeding rate of the certain zone with respect to the current aggregate density, the intended seeding rate, and the target seeding rate. For example, when the difference between the current seeding rate of the certain zone and the current aggregate density is above a specific threshold, such as 30% of the current aggregate density, and when the intended density is less than the target density, the current seeding rate of the certain zone may be increased to be beyond the intended density. In such cases where a yield opportunity exists for a seeding rate that is higher than the intended seeding rate, in step 1612, the system 130 is configured to recommend a fixed or a semi-flex hybrid due to the relatively large density limitation. In other cases where no yield opportunity exists for a seeding rate that is higher than the intended seeding rate, in step 1614, the system 130 is configured to recommend no hybrid change for the static-rate field. In addition, the system 130 may be configured to further determine whether a certain zone may benefit from lower seeding rates from the intended seeding rate. Such a zone may be a risk zone suffering from drought or other natural or environmental attack. Therefore, in step 1616, the system 130 may be configured to recommend a flex hybrid for such a zone corresponding to a relatively low current seeding rate or intended seeding rate to facilitate retainment of water or encourage further crop growth.

Figure 17:
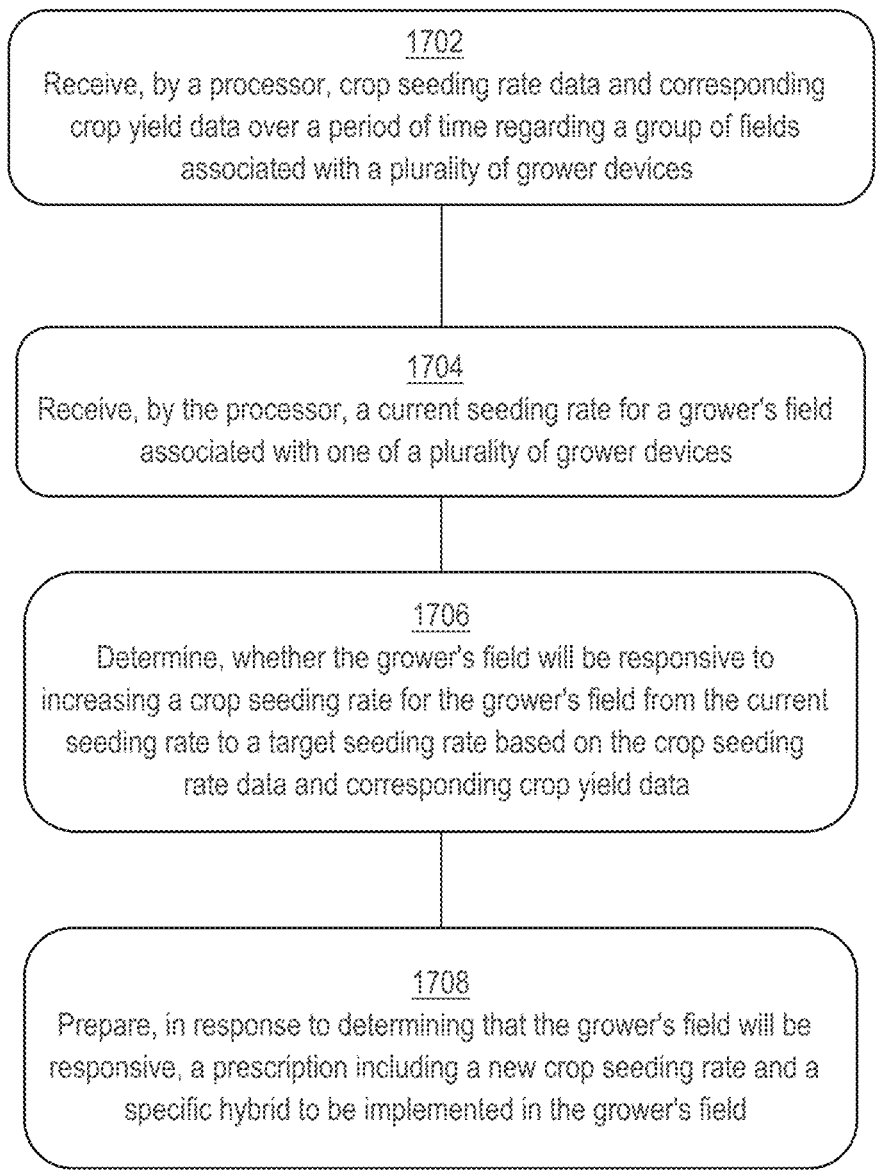
FIG. 17 illustrates an example process performed by the field study server of targeting grower fields for crop yield lift.

FIG. 17 illustrates an example process performed by the agricultural intelligence computer system of targeting grower fields for crop yield lift.

In some embodiments, in step 1702, the system 130 is programmed to receive crop seeding rate data and corresponding crop yield data over a period of time regarding a group of fields associated with a plurality of grower devices. Such data is used to establish benchmarks for determining product responsiveness to a seeding rate increase for a grower's field. The group of fields may be selected from those fields that share values with the grower's field in certain characteristics, such as the crop hybrid grown in a field, the predicted yield lift for a change in management practice for a field, or the location of a field. The time coverage of the data allows the effect of seeding rate increases on the crop yield lift to be revealed. As discussed above, at least an optimal seeding rate and a corresponding threshold on the effect of a seeding rate increase on the crop yield lift can be determined, and more complex approaches can be developed for characterizing or determining the potential impact of a seeding rate change on the crop yield in a grower's field and ultimately whether the grower's field should be targeted for specific experiments to lift the crop yield. In step 1704, the system 130 is programmed to receive a current seeding rate for a grower's field associated with one of a plurality of grower devices. The current seeding rate can be an aggregate across different zones within the field.

In step 1706, the system 130 is programmed to further determine whether the grower's field will be responsive to increasing a crop seeding rate for the grower's field from the current seeding rate to a target seeding rate based on the crop seeding rate data and the corresponding crop yield data. The target seeding rate can be set as the optimal seeding rate or a value that is more consistent with the yield lift management practice for the field or other intent of the grower. Essentially, from the relationship between the seeding rate and the crop yield demonstrated by the group of fields, which can be derived from the crop seeding rate data and the corresponding crop yield data, the system 130 is configured or programmed to estimate an impact of a seeding rate change from the current seeding rate to the target seeding rate in the grower's field and in turn determine whether the grower's field will effectively respond to the seeding rate change by producing the desired crop yield lift.

In step 1708, in response to determining that the grower's field will be responsive, the system 130 is programmed to target the grower's field for an experiment to increase the crop yield and prepare a prescription for the experiment, including a new crop seeding rate and a specific crop hybrid to be implemented in the grower's field. The new crop seeding rate can be the target seeding rate unless it is overridden by an intended seeding rate provided by the grower device. Any recommended change in the crop hybrid is generally consistent with the change in the seeding rate, and it can be implemented incrementally within the field or gradually over time to be able to achieve as much of the estimated crop yield lift as possible. Furthermore, the system 130 can be configured to evaluate the variability in crop yield within the grower's field and prepare a more granular prescription. Such evaluation can be based on physical samples from the field or aerial images of the field. A higher seeding rate than the new seeding rate can often be additionally prescribed to a zone having a seeding rate higher than the current seeding rate. Similarly, a lower seeding rate than the new seeding rate can be additionally prescribed to a zone having a seeding rate lower than the current seeding rate.

As illustrated in FIG. 13, the system 130 can be programed to further collect results of implementing the prescribed experiments from the one grower device or directly from agricultural implements the prescribed the experiments. Specifically, the predicted crop yield lift can be validated against the actual crop yield lift. The system 130 can be configured to then distribute data related to the experiment and the validated results to the other grower devices associated with the group of fields. The seeding rate data and the crop yield data can also be updated with the validated result to enable more accurate modeling of the relationship between crop seeding rates and crop yield.

6. Trial Design

In an embodiment, the agricultural intelligence computing system determines where to place testing locations based on one or more management zones. Management zones refer to regions within an agricultural field or a plurality of agricultural fields that are expected to have similar limiting factors influencing harvested yields of crops. While management zones are generally described with respect to portions of a single field, management zones may be designed to encompass locations in a plurality of fields spanning a plurality of growers. Methods for identifying management zones are described further in U.S. patent application Ser. No. 15/234,943, the entire contents of which is incorporated by reference as if fully disclosed herein. The agricultural intelligence computing system may identify benefits of using a new product, different seeds, and/or management practices for a management zone. The agricultural intelligence computing system may identify testing locations within the management zone so that effects of performing the trial can be compared to the rest of the management zone.

In an embodiment, the agricultural intelligence computing system identifies management zones based on a type of trial being performed. For example, two locations on a field may comprise different soil types, but have a similar yield and a similar pest problem. For purposes of implementing a pesticide trial, the two locations may be treated as a single management zone. In contrast, for purposes of implementing a fertilizer trial which is dependent on the soil type, the two locations may be treated as different zones.

In an embodiment, management zones are identified based on both responsiveness and total yield. The agricultural intelligence computing system may determine the responsiveness of areas in a field to applications of products and/or different management practices based on prior yield data, soil data, imagery, other crop data, and management practices. For example, the agricultural intelligence computing system may identify two equivalent sites where fertilizer was applied on one and not applied on the other. Based on differences in the yield between the two fertilizer rates on equivalent sites, the agricultural intelligence computing system may determine a responsiveness to fertilizer for those and other equivalent locations on the field.

The responsiveness may be a computed value and/or a binary determination. For example, the agricultural intelligence computing system may determine that a location with more than a threshold absolute or percentage change in yield is considered to have high responsiveness while areas with less than the threshold absolute or percentage change in yield is considered to have low responsiveness. The agricultural intelligence computing system may generate zones which have similar responsiveness and similar yields. For example, the agricultural intelligence computing system may generate zones that have high responsiveness and high yield and separate zones that have high responsiveness and low yield, based on yield data, plant data, soil data, weather data, and/or management practice data. Thus, the agricultural intelligence computing system may generate both high responsive zones and low responsive zones that are constrained by total yield.

Within the zones, the agricultural intelligence computing system may identify possible locations for testing locations. The size and shape of testing locations may be determined based on variability in a particular field or zone. Variability, as used herein, refers to the amount the total yield tends to vary within a field and/or management zone. The amount of variance may include both magnitude of variance and a spatial component of the variance. For example, if the yield fluctuates rapidly within a small region of a management zone, the agricultural intelligence computing system may determine that a larger testing location should be implemented. In contrast, if the yield has long length scale trends in yield, a smaller testing location may be implemented. The optimal size, shape, and number of testing locations can be determined directly from historic yield variability data. In one embodiment, the historic yield data is broken into uniform grids of potential testing locations different sizes; the total testing area required, including buffer areas around testing locations, is calculated for each testing location size given an acceptable statistical significance for the answer; and the optimal configuration is the one that minimizes the total testing area. The optimal size, shape, and number of testing locations can also be determined from modeled yield variability data from historic images, or modeled yield variability data based on predictors to a model trained on historic yield variability data. Further, based on the size of testing location, the agricultural intelligence computing system may identify a shape of the testing location in order to maximize a number of testing locations that can be fit into a single zone. For example, if a zone is particularly narrow, the agricultural intelligence computing system may select a narrow rectangle as the shape of the testing location.

Using the identified size and shape of the testing locations, the agricultural intelligence computing system may determine a plurality of possible locations for placing the testing locations in the field. The agricultural intelligence computing system may then select a subset of the plurality of possible locations for placing the testing locations. In an embodiment, the agricultural intelligence computing system determines a number of testing locations to implement based on trial requirements and/or user selection. For example, a constraint of a trial may be that at least two testing locations are planted in each management zone. As another example, a field manager may indicate, through a graphical user interface executing on the field manager computing device, that the field manager is willing to dedicate five percent of the field to the trial. The agricultural intelligence computing system may thus compute the number of testing locations as:

$$N = A*D/A_T$$

where N is the number of testing locations, A is the area of the field, D is the percentage of the field dedicated to trials, and A is the area of the testing locations. As another example, a field manager may indicate, through a graphical user interface executing on the field manager computing device, that the field manager wants to detect a minimum treatment effect of a certain number of bushels per acre with a given signal to noise ratio. The agricultural intelligence computing system may thus compute the number of testing locations as:

$$N = (SNR*\sigma/T)^2$$

where N is the number of testing locations, SNR is the signal to noise ratio, σ is the standard deviation of the average yield difference between potential testing locations, and T is the desired minimum detectable treatment effect.

In an embodiment, the agricultural intelligence computing system randomly selects locations of the plurality of potential locations until the determined number of testing locations have been identified. The agricultural intelligence computing system may constrain the random selection by selecting at least two locations for a zone where a first location is selected, thereby allowing for both a test group and a control group. The agricultural intelligence computing system may also constrain the random selection to ensure that testing locations are placed in a maximum number of zones. Additionally or alternatively, the agricultural intelligence computing system may present, through a graphical user interface on the field manager computing device, a plurality of possible locations for testing locations. The field manager may select particular locations of the plurality of possible locations and send the selections to the agricultural intelligence computing system.

In an embodiment, the agricultural intelligence computing system selects locations for the testing locations in order to minimize the effect on total yield from performing the trial. For example, the agricultural intelligence computing system may prioritize areas of the field that have had historically lower yields, thereby reducing any possible negative impacts on the yield of the field. Additionally or alternatively, the agricultural intelligence computing system may prioritize location for the testing locations in a manner that maximizes benefit of performing the trials. For example, for a pesticide trial the agricultural intelligence computing system may select regions of the field that have historically received the highest negative impact on yield due to pests.

The prioritizations based on minimizing the effect on yield or maximizing the benefits of performing the trials may be implemented along with other constraints. For example, the agricultural intelligence computing system may initially attempt to place at least two testing locations in each management zone. The agricultural intelligence computing system may then pseudo-randomly select additional testing locations while assigning higher weights to locations with low yields or high responsiveness. As another example, the agricultural intelligence computing system may attempt to place testing locations in a minimum of a high responsiveness and high yield location, a high responsiveness and low yield location, a low responsiveness and high yield location, and a low responsiveness and low yield location.

Figure 8:
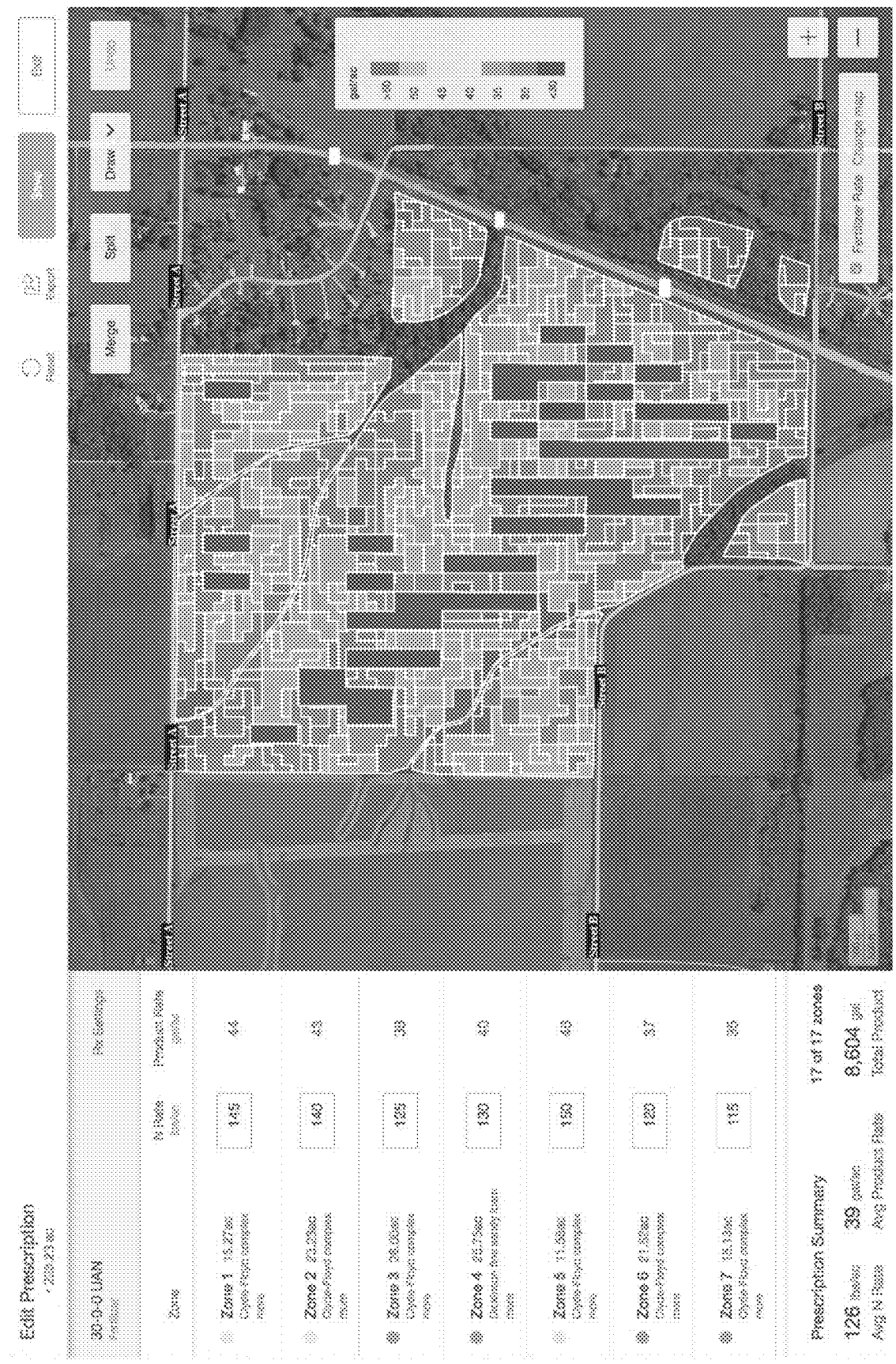
FIG. 8 depicts an example of implementing testing locations on a field.

FIG. 8 depicts an example of implementing testing locations on a field. The field of FIG. 8 is broken up into different management zones, each marked by a color. Dark brown polygons depict possible testing locations. In embodiments, they are placed to span management zones. In embodiments, adjacent polygons with the same management may be merged. In embodiments, of the possible testing locations, the agricultural intelligence computing system randomly selects locations to implement the testing locations. In embodiments, the agricultural intelligence computing system selects locations according to one or more constraints. For example, in FIG. 8, a possible constraint is a minimum location width of 120 feet to be compatible with field manager equipment. Another is that at least 40 testing locations are implemented in this field to achieve a predicted minimum significant detectable treatment effect. Additionally, in FIG. 8 the testing locations are implemented such that each has an unmarked control location randomly assigned to the equivalently sized area on one or the other of its two long sides.

7. Field Manager Computing Device Communication

The agricultural intelligence computing system may send the trial participation request to a graphical user interface on the field manager computing device. The trial participation request may identify the constraints of the trial and one or more values associated with the trial. The value association is described further herein. The graphical user interface may include options for agreeing to participate in the trial, selecting a particular amount of a field to dedicate to the trial, selecting the degree of change in management practices, and/or selecting the desired confidence level of the results. The agricultural intelligence computing system may identify possible locations in the field for implementing testing locations for the trial. Additionally or alternatively, the graphical user interface may include options for selecting placement of the testing locations.

In an embodiment, the trial participation request does not directly identify a product or management practice to the field manager computing device. For example, the trial participation request may identify that different hybrid seeds are to be used in a trial location, but not identify the type of hybrid seeds. The hybrid seeds may be physically sent to the field for implementation of the trial. Thus, the field manager may execute the trial without knowledge of the type of seed being planted, a type of product being applied, or one or more management practices being applied as part of the trial.

Figure 9:
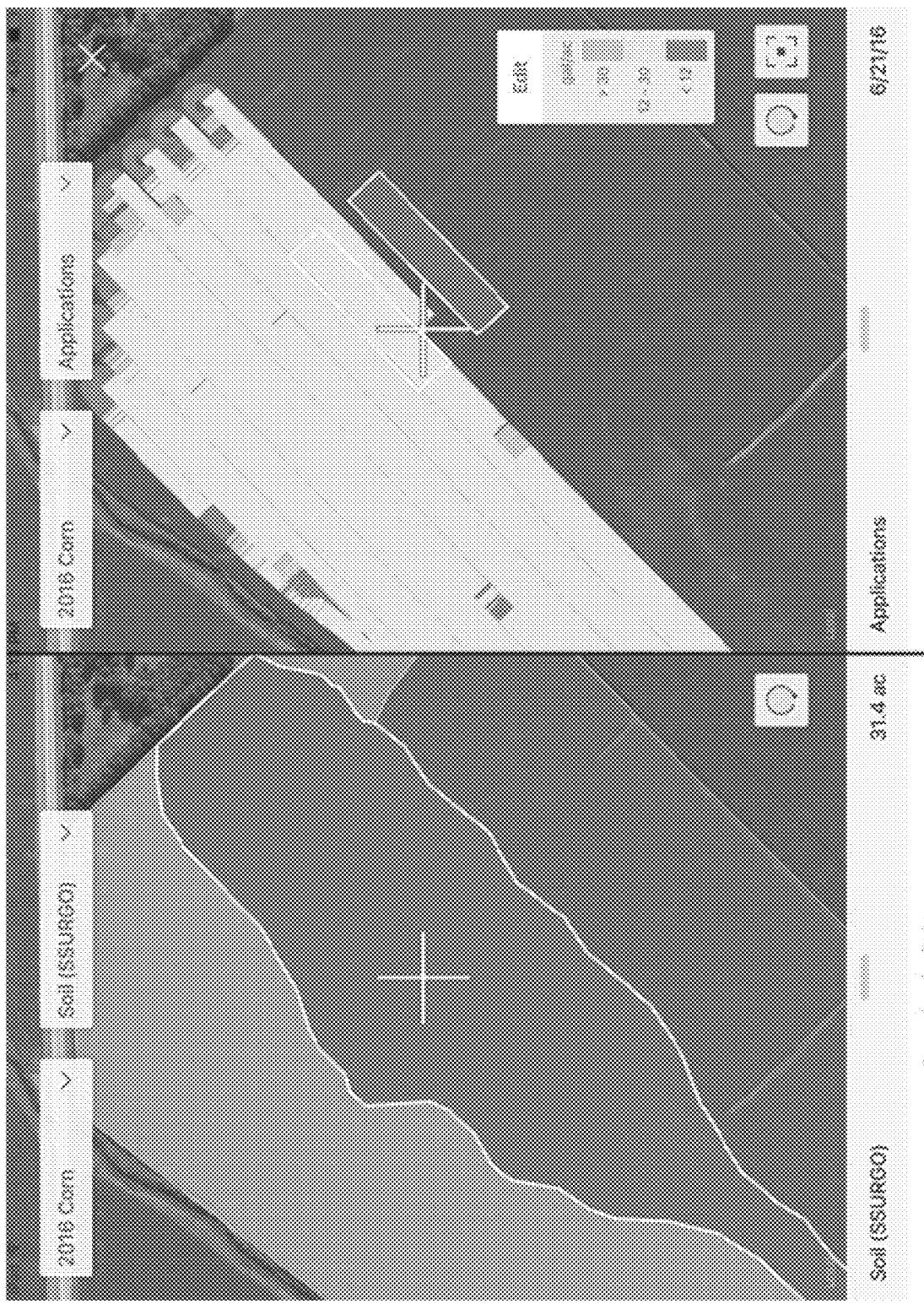
FIG. 9 depicts a graphical user interface for selecting locations to place testing locations.

FIG. 9 depicts a graphical user interface for selecting locations to place testing locations. In the leftmost image of FIG. 9, the field is separated into multiple zones based on soil type. In the rightmost image shows application rates of nitrogen by location. One location has been selected for implementing a testing location where nitrogen has been applied while a second location has been selected for implementing a testing location where nitrogen has not been applied, thereby acting as a control group. Both locations are within the same management zone.

Figure 10:
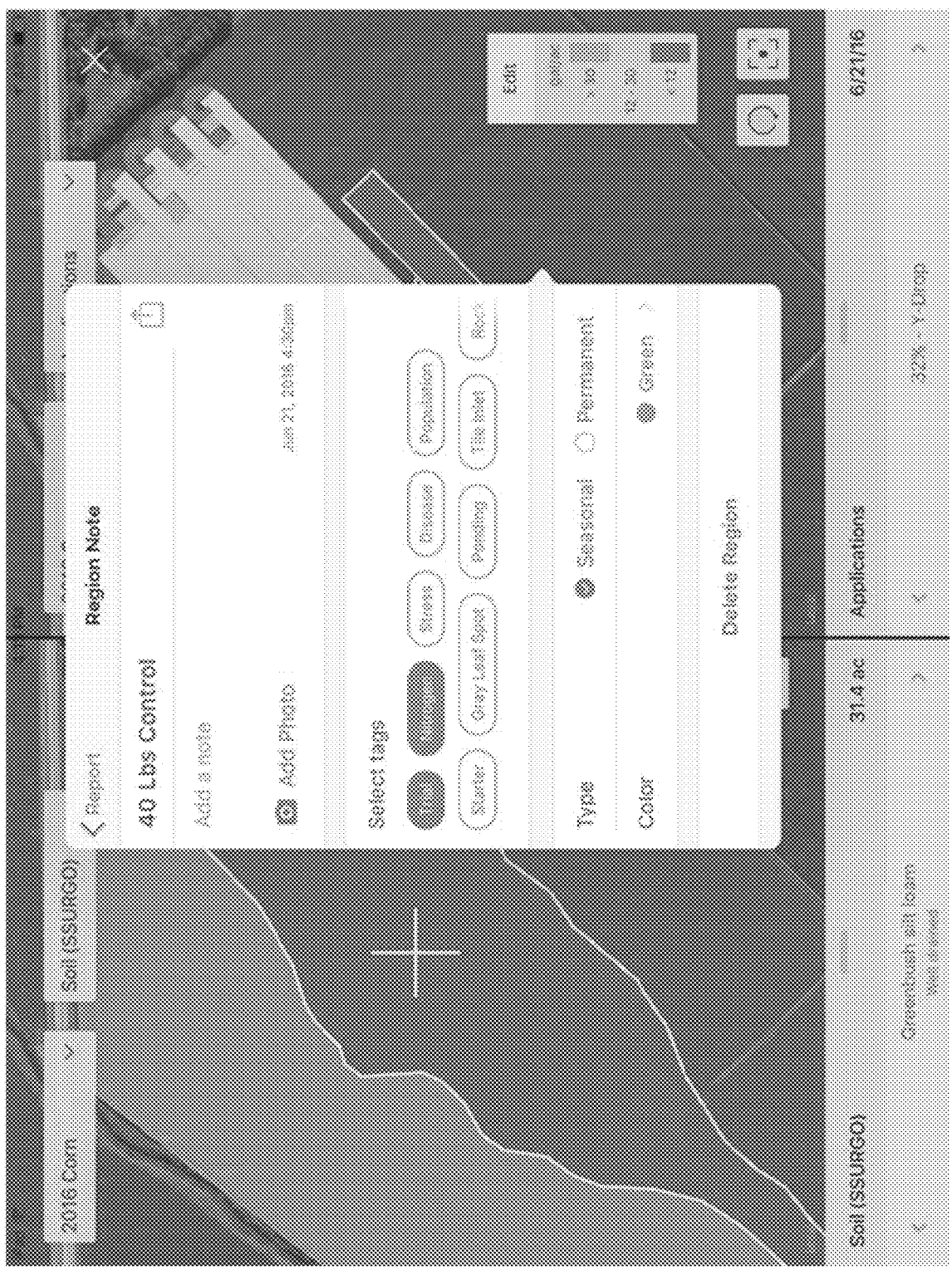
FIG. 10 depicts an example graphical user interface for defining selected locations.

The graphical user interface executing on the field manager computing device may include options for naming, describing, and tagging selected locations. FIG. 10 depicts an example graphical user interface for defining selected locations. The display of FIG. 10 includes a text box for naming the selected location, a text box for adding a description of the selected location, and an option to select one or more tags for the selected location. The tags may be used later for searching through prior selected locations. For instance, if the field manager implements a plurality of different types of trials, the field manager may use the tags to identify locations that have been tagged for a particular type of trial. While FIG. 10 is described in terms of a user interface, similar tags may be used by the agricultural intelligence computing system to track regions of the field with particular trials.

Figure 11:
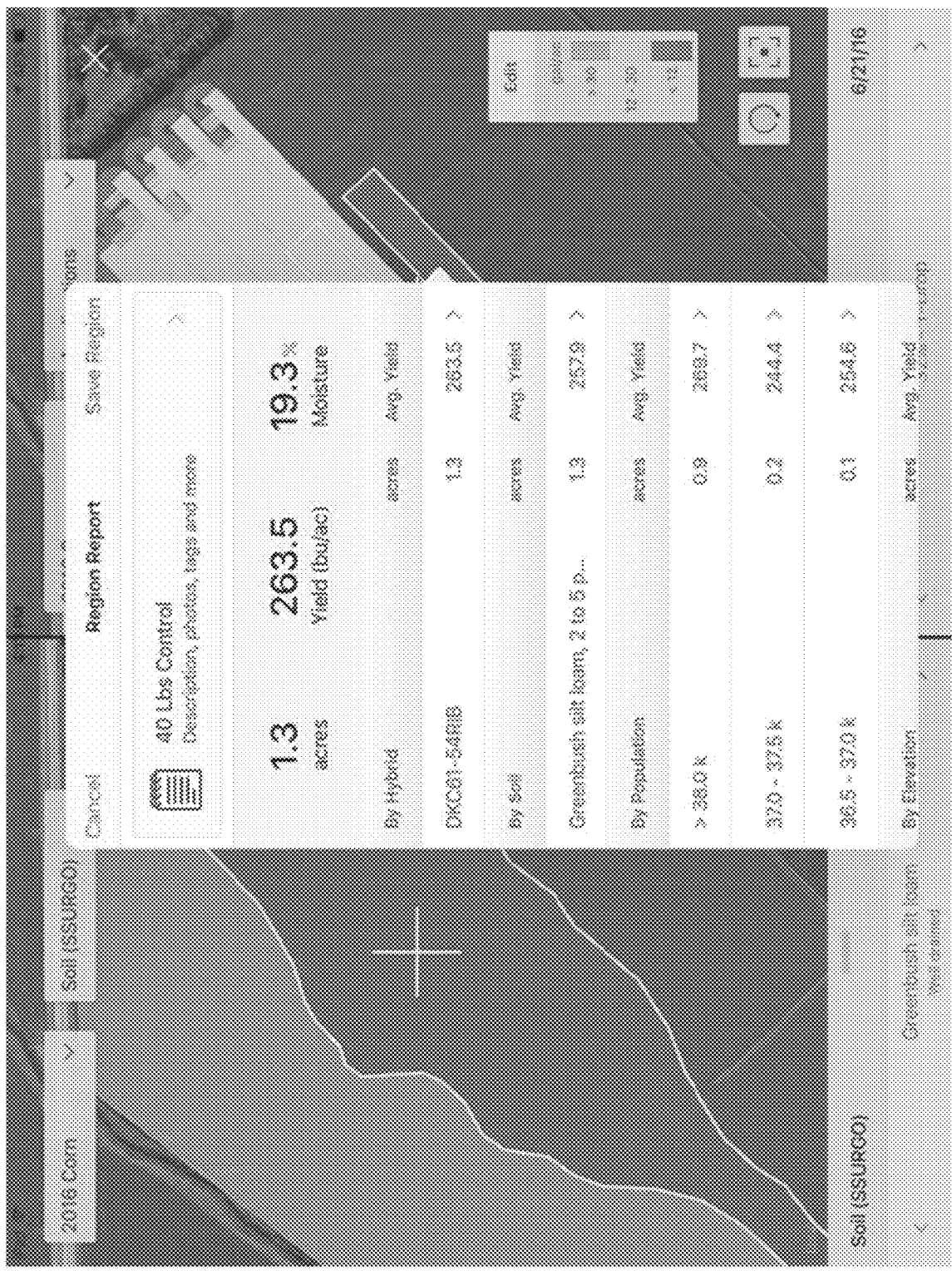
FIG. 11 depicts an example graphical user interface for displaying information pertaining to a selected region.

Once a region has been selected, the agricultural intelligence computing system may track and cause display of information pertaining to the selected region. FIG. 11 depicts an example graphical user interface for displaying information pertaining to a selected region. In FIG. 11, the "40 Lbs Control" region has been selected. The report depicts a yield for the location, a soil moisture of the location, as well as statistics relating to subregions of the selected region. For instance, the average yield for the "Population >38.0 k seeds per acre" subregion is depicted under the average yield for the selected location. In another embodiment, the report could depict yield for other locations, for instance, the average yield for "Population >38.0 k seeds per acre" in the trial region, or in the remainder of the field outside the "40 Lbs Control" region.

Figure 12:
FIG. 12 depicts an example graphical user interface for depicting results of a trial.

The server may additionally display comparisons between trial data, control data, and other field data. FIG. 12 depicts an example graphical user interface for depicting results of a trial. FIG. 12 identifies average yields for each type of trial as compared to the average yield for the field. The interface of FIG. 12 depicts example yields for the nitrogen control, nitrogen trial, and a late season nitrogen application trial. The interface provides an easy visual verification of the effects on implementing the trial. A vertical line may also depict the average yield for the entire field.

In an embodiment, the agricultural intelligence computing system initially tracks progress of implementing the testing locations within the field. For example, a field sensor may indicate where a field implement has been planting crops or applying products. As the field implement plants seeds within an area selected as a testing location, the agricultural intelligence computing system may monitor the planting and/or applications in order to determine if the testing location is in compliance with requirements of the trial. For example, a trial may require that a testing location include a requirement for a planting population of 35,000 seeds per acre. If the agricultural intelligence computing system receives data indication that an implement has planted 35,000 seeds per acre in a particular testing location, the agricultural intelligence computing system may indicate to the field manager that the testing location has been correctly implemented. As an example, a color of the testing location on a map displayed on the field manager computing device may change in response to the server determining that the testing location meets the requirements of the trial.

As the server tracks the planting and/or application of a field implement, the agricultural intelligence computing system may send warnings to a field manager computing device indicating that the field implement is about to begin planting or application in a testing location. For example, the server may track the planting of a first hybrid seed by a planting implement on a particular field. If the testing location requires the planting of a second hybrid seed, the agricultural intelligence computing system may send a warning to the field manager computing device as the planting implement nears the testing location. The warning allows the field manager to stop the planting implement before the planting implement invalidates the testing location for the trial.

Additionally or alternatively, the agricultural intelligence computing system may send instructions that, if executed, cause a field implement to correct planting or applications in the testing location. For example, the agricultural intelligence computing system may send a script that can be used to control a field implement to cause the field implement to implement the trial. The agricultural intelligence computing system may send the script directly to a field manager computing device controlling the implement, thereby automatically compensating for incorrect planting or applications. Additionally or alternative, the agricultural intelligence computing system may send the script to a field manager computing device that is then used by a field manager to compensate for planting or applications.

In an embodiment, the agricultural intelligence computing system offers alternatives if the agricultural intelligence computing system determines that a testing location has been invalidated. When a testing location has been invalidated, the agricultural intelligence computing system may identify one or more additional locations for implementing the testing location. The agricultural intelligence computing system may cause display, through the graphical user interface executing on the field manager computing device, an identification of one or more alternative locations for implementing the testing location. In an embodiment, the graphical user interface may include options for the field manager to select one of the alternative locations for implementing the testing location. In another embodiment, the agricultural intelligence computing system may cause, through the application controller, the agricultural apparatus to automatically implement the testing location at an alternative location without requiring action from the field manager.

As an example, a first testing location may be defined at a first location as a control group which does not receive a nitrogen application. If the agricultural intelligence computing system determines that nitrogen has been applied to the first location, the agricultural intelligence computing system may identify one or more second locations where nitrogen has not been applied. The agricultural intelligence computing system may cause display of the one or more second locations on the field manager computing device. In response to receiving a selection of a particular location, the agricultural intelligence computing system may update the map to indicate that the particular location is a second testing location that is defined as a control group which does not receive a nitrogen application. The agricultural intelligence computing system may then send warnings to the field manager computing device to not apply nitrogen to the particular location.

As another example, a first testing location may be defined at a first location as a control group which does not receive a nitrogen application. If the agricultural intelligence computing system determines that nitrogen has been applied to the first location, the agricultural intelligence computing system may identify one or more second locations where nitrogen has not been applied. The agricultural intelligence computing system may cause, directly through the application controller, the agricultural apparatus to automatically implement the testing location at an alternative location without requiring action from the field manager. The agricultural apparatus may then not apply nitrogen to the particular location.

In an embodiment, the agricultural intelligence computing system may be programmed or configured to alter one or more trials in response to determining that a testing location does not comply with a trial. In an embodiment, the agricultural intelligence computing system suggests alterations to one or more practices for other locations to offset errors in the testing location. For example, if a control location was planted with a seeding rate that is ten percent higher than required by the trial, the agricultural intelligence computing system may modify the seeding rate for the other testing locations to be ten percent higher.

The agricultural intelligence computing system may additionally alter the predicted results of the trial based on identified modifications to the testing locations. For example, the agricultural intelligence computing system may predict an increase in yield of 30 bushels/acre for an application of 40 lbs/acre of nitrogen. If the agricultural intelligence computing system detects that only 30 lbs/acre of nitrogen has been applied to a field, the agricultural intelligence computing system may lower the predicted increase in yield of 30 bushels/acre.

The agricultural intelligence computing system may additionally use observed field data to determine if a field is in compliance with a trial. For example, the agricultural intelligence computing system may compare results of the trial to results of equivalent trials on other fields and/or average results for a geographic region, such as a county. If the results of the trial vary widely from the results of the other field or geographic region, the agricultural intelligence computing system may determine that the trial was incorrectly implemented on the field.

8. Value Association

In an embodiment, the agricultural intelligence computing system associates a result value with performance of the trial. The associated result value may be a reduced cost for obtaining products, a cost to the field manager if the trial is successful, a rebate if the trial is unsuccessful, carbon credits, water use credits, and/or any form of digital currency.

In an embodiment, the trial participation request includes a commitment to a particular outcome, such as an absolute yield, a revenue, a percent increase of income or revenue based on yield, and/or a quality of the crop. For example, the trial participation request may include a guarantee that the total yield for a field will increase by 20 bushels/acre if a particular pesticide is used on the field. If the field manager agrees to participate in the trial, the field manager is required to use the pesticide in one or more testing locations and not use the pesticide in one or more control locations. If the testing location outperforms the control location by at least 20 bushels/acre, the agricultural intelligence computing system will determine that the guaranteed outcome has occurred. If the testing location does not outperform the control location by at least 20 bushels/acre, the agricultural intelligence computing system may determine that the guaranteed outcome has not occurred.

In an embodiment, the trial participation request may offer a product or seed at a discount or for free in return for participation in the trial and a portion of profit if the guaranteed outcome occurs. For example, a trial participation offer may include free seeds of a particular hybrid for a farmer, but a promise that if the yield increase for the testing locations exceed 20 bushels/acre, the field manager must pay ten percent of the increase in revenue and/or return on investment from the sale of the crop. The portion of profit may be a portion of actual profit or modeled profit based on average prices for the harvested crop.

While embodiments have been described generally with respect to planting of seeds or application of a product, a similar trial participation request may be based on different management practices. For example, the agricultural intelligence computing system may receive data from a field manager computing device indicating historical management practices and historical yield. The agricultural intelligence computing system may compute a benefit of changing one or more management practices. The agricultural intelligence computing system may send a trial participation request that indicates that the agricultural intelligence computing system has identified one or more management practices which, if altered, would guarantee a particular benefit. If the field manager computing device agrees to participate in the trial, the agricultural intelligence computing system may send the one or more changed management practices to the field manager computing device. If testing locations that implement the changed management practices benefit by the guaranteed amount, the agricultural intelligence computing system may request a portion of revenue and/or return on investment. For example, the agricultural intelligence computing system may compute a benefit of changing from fall nitrogen fertilizer application to spring nitrogen fertilizer application. If testing locations that implement the spring nitrogen fertilizer application benefit by the guaranteed amount, the agricultural intelligence computing system may request a portion of increased revenue and/or return on investment.

While embodiments have been described generally with respect to planting of seeds or application of a product or different management practices, a similar trial participation request may be based on different farming equipment. For example, the agricultural intelligence computing system may receive data from a field manager computing device indicating historical management practices, historical farming equipment, and historical yield. The agricultural intelligence computing system may compute a benefit of changing one or more farming equipment pieces. The agricultural intelligence computing system may send a trial participation request that indicates that the agricultural intelligence computing system has identified one or more farming equipment pieces which, if altered, would guarantee a particular benefit. If the field manager computing device agrees to participate in the trial and the farming equipment dealer agrees to participate in the trial, the agricultural intelligence computing system may send one or more changed management practices to the field manager computing device and to the farming equipment dealer. If testing locations that implement the changed farming equipment benefit by the guaranteed amount, the agricultural intelligence computing system may request a portion of revenue and/or return on investment from the farm manager or from the farming equipment dealer. For example, the agricultural intelligence computing system may compute a benefit of changing to new planting equipment. If testing locations that implement the new planting equipment benefit by the guaranteed amount, the agricultural intelligence computing system may request a portion of increased revenue, return on investment, or equipment sale price.

Additionally or alternatively, the agricultural intelligence computing system may offer a rebate if the guaranteed increase in yield does not occur. For example, the agricultural intelligence computing system may charge for a particular product or for providing management practice advice. The agricultural intelligence computing system may guarantee a particular increase in yield based on use of the provided management practice device or particular product. The agricultural intelligence computing system may additionally offer a rebate if the guaranteed particular increase in yield does not occur. Thus, a field manager may be assured that either the field manager will receive a substantial benefit for participating in the trial or at least a portion of the costs of participating in the trial will be recoverable.

In an embodiment, the agricultural intelligence computing system determines the result value association based on captured data for the field. For example, the agricultural intelligence computing system may receive field data including field descriptions, soil data, planting data, fertility data, harvest and yield data, crop protection data, pest and disease data, irrigation data, tiling data, imagery, weather data, and additional management data. Based on the field data, the agricultural intelligence computing system may compute benefits to the field of using one or more products, management practices, farming equipment, or seeds. The agricultural intelligence computing system may generate a trial participation request based on the computed benefits to the field. For example, the agricultural intelligence computing system may be programmed or configured to offer the one or more products, management practices, farming equipment, or seeds at a particular percentage of computed increase in profits for the field.

As an example, an agricultural intelligence computing system may determine that applying a particular management practice would increase the yield of a field by 20 bushels/acre. The agricultural intelligence computing system may also determine that the price of the crop is roughly $4 per bushel. Thus, the expected increase in profit for implementing the management practice would be $80/acre. If the agricultural intelligence computing system is programmed or configured to request 10% of expected profits, the agricultural intelligence computing system may send a trial participation request that guarantees an increase in yield of 15 bushels/acre at a cost of $8 per acre applied.

In an embodiment, the agricultural intelligence computing system determines the result value association based on a risk tolerance associated with the field manager computing device. The risk tolerance may be determined using any of the methods described herein. If the risk tolerance associated with the field manager computing device is higher than a particular value, the agricultural intelligence computing system may offer a relatively high initial price with a relatively high rebate for failure to meet the condition. If the risk tolerance associated with the field manager computing device is lower than a particular value, the agricultural intelligence computing system may offer a relatively low initial price with a relatively low rebate for failure to meet the condition.

In an embodiment, the agricultural intelligence computing system sets a plurality of result values to be associated with the trial participation request. For example, the trial participation request may include a tiered rebate system where a first rebate is paid out if the trial benefited the yield, but not to the extent guaranteed by the trial participation request and a second rebate is paid out if the trial did not benefit the yield. Other tier levels may be set based on the level of benefit of the trial. For example, a tiered system may set different rebate values for each 5 bushels/acre below the guaranteed yield.

Result value association may be based on individual trial locations or on a combination of trial locations. For example, the trial participation request may include an offer based on an average performance of all testing locations participating in the trial. Thus, one of the testing locations producing a yield lower than the guaranteed yield may not indicate a failure of the trial as long as the average yield for the testing locations is above the guaranteed yield. As another example, the trial participation request may include an offer based on an average performance of all testing locations from multiple operations participating in the trial in a geographic region, like a county.

In an embodiment, the trial participation request offer's region of average performance used to determine the trial benefits may be determined based on a risk tolerance associated with the field manager computing device. If the risk tolerance associated with the field manager computing device is higher than a particular value, the agricultural intelligence computing system may offer a relatively small region of average performance, potentially subfield including to the individual testing location level. If the risk tolerance associated with the field manager computing device is lower than a particular value, the agricultural intelligence computing system may offer a relatively large region of average performance, potentially including testing locations in fields spanning multiple field managers and even farming operations across a geographic area like a county.

In an embodiment, the result value association includes a guaranteed margin for the field manager. For example, the agricultural intelligence computing system may model a likely yield and/or a likely revenue from using one or more seeds, one or more products, and/or one or more management practices. The agricultural intelligence computing system may guarantee a revenue for the field manager based on the modeled yield and/or likely revenue. If the field manager computing device agrees to the trial, the field manager may be provided with the one or more seeds, one or more products, and/or one or more management practices. Upon completion of the trial, the agricultural intelligence computing system may compute a result value comprising a difference between a predicted and/or actual revenue and the guaranteed revenue. The computed result value may represent an amount due from the field manager. If the computed result value is negative, then the computed result value indicates an amount owed to the field manager. Thus, the trial participation request is able to ensure a particular profit for the field manager while still being beneficial for the trial requester.

In an embodiment, the associated result value may be based on a portion of the field assigned to the trial. For example, the agricultural intelligence computing system may generate different levels of rebates based on the percentage or acreage of the field that the field manager agrees to use for the trial. A first rebate value may be set for a first percentage or amount of the field assigned to the trial and a second higher rebate value may be set for a second higher percentage or amount of the field assigned to the trial. Thus, the field manager is incentivized to increase the amount of the field dedicated to the trial in order to be able to claim the higher benefits and/or rebates.

9. Benefits of Certain Embodiments

Using the techniques described herein, a computer can track practices across a plurality of fields, identify fields that would benefit from performing a trial, identify locations for performing trials, and incentivize participation in the trials. The techniques described herein may additionally be used to automate machinery on a particular field. For example, upon determining a testing location on a field and receiving from the field manager computing device an agreement to participate in the trial, the agricultural intelligence computing system may generate one or more scripts for field implements that cause the field implements to plant seeds, apply products, or perform particular management practices in accordance with the trial. Additionally, by monitoring field implements in real-time, an agricultural intelligence computing system may be able to identify incorrect applications before they occur and/or identify alternatives in response to an incorrect application. Thus, the methods described herein may improve the agricultural intelligence computing system's ability to interact with the field manager computing device over a network and provide real-time solutions.

10. Extensions and Alternatives

In the foregoing specification, embodiments have been described with reference to numerous specific details that may vary from implementation to implementation. The specification and drawings are, accordingly, to be regarded in an illustrative rather than a restrictive sense. The sole and exclusive indicator of the scope of the disclosure, and what is intended by the applicants to be the scope of the disclosure, is the literal and equivalent scope of the set of claims that issue from this application, in the specific form in which such claims issue, including any subsequent correction.

What is claimed is:

1. A computer-implemented method, comprising:
based on an agricultural implement performing an agricultural activity with respect to one or more target agricultural fields of a plurality of agricultural fields:
receiving data corresponding to the agricultural activity from one or more field sensors or one or more sensors integrated with the agricultural implement;
determining, based on the received data, compliance of the one or more target agricultural fields with a trial;
in response to determining that the one or more target agricultural fields are not in compliance with the trial, generating a warning at a cab computer associated with the agricultural implement, the warning indicating that the one or more target agricultural fields are not in compliance with the trial; and
adjusting, by the cab computer associated with the agricultural implement, based on the trial for the one or more target agricultural fields, the agricultural activity being performed by the agricultural implement with regard to the one or more target agricultural fields.

2. The computer-implemented method of claim 1, wherein generating the warning includes causing displaying, through a graphical user interface executing on a field manager computing device, the warning.

3. The computer-implemented method of claim 1, wherein adjusting the agricultural activity being performed by the agricultural implement includes correcting planting activity being performed by the agricultural implement in the one or more target agricultural fields, so that the one or more target agricultural fields are in compliance with the trial.

4. The computer-implemented method of claim 1, wherein adjusting the agricultural activity being performed by the agricultural implement includes correcting an application being performed by the agricultural implement in the one or more target agricultural fields, so that the one or more target agricultural fields are in compliance with the trial.

5. The computer-implemented method of claim 1, wherein adjusting the agricultural activity being performed by the agricultural implement includes correcting the agricultural activity being performed by the agricultural implement while the agricultural implement is in the one or more target agricultural fields, to thereby bring the one or more target agricultural fields into compliance with the trial.

6. The computer-implemented method of claim 1, wherein adjusting the agricultural activity being performed by the agricultural implement includes modifying operation of the agricultural implement while the agricultural implement is in the one or more target agricultural fields, to thereby bring the one or more target agricultural fields into compliance with the trial.

7. The computer-implemented method of claim 1, wherein adjusting the agricultural activity being performed by the agricultural implement includes stopping operation of the agricultural implement prior to the agricultural implement performing the agricultural activity in the one or more target agricultural fields.

8. The computer-implemented method of claim 1, further comprising, in response to the warning, identifying one or more additional locations of the one or more target agricultural fields which would allow the one or more target agricultural fields to be in compliance with the trial.

9. A system, comprising:
an agricultural intelligence computing system having one or more processors;
a memory storing instructions which, when executed by the one or more processors of the agricultural intelligence computing system, cause the one or more processors to:
based on an agricultural implement performing an agricultural activity with respect to one or more target agricultural fields of a plurality of agricultural fields:
receive data corresponding to the agricultural activity from one or more field sensors or one or more sensors integrated with the agricultural implement;
determine, based on the received data, a compliance of the one or more target agricultural fields with a trial; and
in response to determining that the one or more target agricultural fields are not in compliance with the trial, generate a warning indicating that the one or more target agricultural fields are not in compliance with the trial; and
a non-transitory computer-readable storage medium comprising executable instructions, which when executed by at least one processor of a cab computer associated with the agricultural implement, cause the at least one processor of the cab computer to, in response to the warning, adjust the agricultural activity being performed by the agricultural implement with regard to the one or more target agricultural fields.

10. The system of claim 9, wherein the instructions, when executed by the one or more processors of the agricultural intelligence computing system, further cause the one or more processors to transmit the warning to a field manager computing device.

11. The system of claim 10, further comprising a non-transitory computer-readable storage medium comprising executable instructions, which when executed by at least one processor of the field manager computing device, cause the at least one processor of the field manager computing device to display the warning through a graphical user interface executing on the field manager computing device.

12. The system of claim 11, wherein the warning includes an icon displayed on a map of the one or more target agricultural fields.

13. The system of claim 9, wherein the instructions, when executed by the one or more processors of the agricultural intelligence computing system, further cause the one or more processors to stop operation of the agricultural implement prior to the agricultural implement performing the agricultural activity in the one or more target agricultural fields.

14. The system of claim 9, wherein the instructions, when executed by the one or more processors of the agricultural intelligence computing system, further cause the one or more processors to modify operation of the agricultural implement while the agricultural implement is in the one or more target agricultural fields, to thereby bring the one or more target agricultural fields into compliance with the trial.

15. The system of claim 9, wherein the instructions, when executed by the one or more processors of the agricultural intelligence computing system, further cause the one or more processors to, in response to the warning, identify one or more additional locations of the one or more target agricultural fields which would allow the one or more target agricultural fields to be in compliance with the trial.

16. The system of claim 9, wherein the agricultural activity includes planting activity and/or treatment activity.

\* \* \* \* \*